US012721867B2

(12) United States Patent
Perin et al.

(10) Patent No.: US 12,721,867 B2
(45) Date of Patent: Sep. 1, 2026

(54) EXTRACELLULAR VESICLES FROM STEM CELLS TO TREAT AND/OR PREVENT DISEASE

(71) Applicants: Children's Hospital Los Angeles, Los Angeles, CA (US); Benedetta Bussolati, Turin (IT)

(72) Inventors: Laura Perin, Burbank, CA (US); Sargis Sedrakyan, Glendale, CA (US); Benedetta Bussolati, Turin (IT); Roger De Filippo, Glendale, CA (US)

(73) Assignee: Children's Hospital Los Angeles, Los Angeles, CA (US)

( * ) Notice: Subject to any disclaimer, the term of this patent is extended or adjusted under 35 U.S.C. 154(b) by 0 days.

(21) Appl. No.: 16/348,412

(22) PCT Filed: Nov. 9, 2017

(86) PCT No.: PCT/US2017/060917

§ 371 (c)(1),
(2) Date: May 8, 2019

(87) PCT Pub. No.: WO2018/089672

PCT Pub. Date: May 17, 2018

(65) Prior Publication Data

US 2020/0121729 A1 Apr. 23, 2020

Related U.S. Application Data

(60) Provisional application No. 62/419,812, filed on Nov. 9, 2016.

(51) Int. Cl.

| | |
|---|---|
| ***A61K 35/50*** | (2015.01) |
| ***A61K 9/00*** | (2006.01) |
| ***A61K 35/545*** | (2015.01) |
| ***A61P 13/12*** | (2006.01) |

(52) U.S. Cl.
CPC ............ *A61K 35/50* (2013.01); *A61K 9/0019* (2013.01); *A61K 35/545* (2013.01); *A61P 13/12* (2018.01)

(58) Field of Classification Search
CPC ........ A61K 35/50; A61K 9/0019; A61P 13/12
See application file for complete search history.

(56) References Cited

U.S. PATENT DOCUMENTS

| | | | |
|---|---|---|---|
| 2010/0196426 | A1 | 8/2010 | Skog et al. |
| 2014/0044647 | A1 | 2/2014 | Gho et al. |

FOREIGN PATENT DOCUMENTS

| | | | |
|---|---|---|---|
| WO | WO-2018089672 A1 | 5/2018 | |

OTHER PUBLICATIONS

Marote A, Teixeira FG, Mendes-Pinheiro B, Salgado AJ. MSCs-Derived Exosomes: Cell-Secreted Nanovesicles with Regenerative Potential. Front Pharmacol. 2016;7:231. (Year: 2016).*

Zou X, Zhang G, Cheng Z, Yin D, Du T, Ju G, Miao S, Liu G, Lu M, Zhu Y. Microvesicles derived from human Wharton's Jelly mesenchymal stromal cells ameliorate renal ischemia-reperfusion injury in rats by suppressing CX3CL1. Stem cell research & therapy. Jun. 2014;5(2): 1-3. (Year: 2014).*

Choi HY, Moon SJ, Ratliff BB, Ahn SH, Jung A, Lee M, Lee S, Lim BJ, Kim BS, Plotkin MD, Ha SK. Microparticles from kidney-derived mesenchymal stem cells act as carriers of proangiogenic signals and contribute to recovery from acute kidney injury. PloS one. Feb. 4, 2014;9(2):e87853 (Year: 2014).*

Sanchez MB, Bruno S, Grange C, Tapparo M, Cantaluppi V, Tetta C, Camussi G. Human liver stem cells and derived extracellular vesicles improve recovery in a murine model of acute kidney injury. Stem cell research & therapy. Dec. 2014;5(6):1-1. (Year: 2014).*

Cantaluppi et al. Microvesicles derived from endothelial progenitor cells protect the kidney from ischemia-reperfusion injury by micro RNA-dependent reprogramming of resident renal cells. Kidney international. Aug. 2, 2012;82(4):412-27. (Year: 2012).*

Zhou Y, Xu H, Xu W, Wang B, Wu H, Tao Y, Zhang B, Wang M, Mao F, Yan Y, Gao S. Exosomes released by human umbilical cord mesenchymal stem cells protect against cisplatin-induced renal oxidative stress and apoptosis in vivo and in vitro. Stem cell research & therapy. Jun. 2013;4(2):1-3. (Year: 2013).*

Gatti S, Bruno S, Deregibus MC, Sordi A, Cantaluppi V, Tetta C, Camussi G. Microvesicles derived from human adult mesenchymal stem cells protect against ischaemia-reperfusion-induced acute and chronic kidney injury. Nephrol Dial Transplant. May 2011;26(5): 1474-83. (Year: 2011).*

Abels ER, Breakefield XO. Introduction to Extracellular Vesicles: Biogenesis, RNA Cargo Selection, Content, Release, and Uptake. Cell Mol Neurobiol. Apr. 2016;36(3):301-12. (Year: 2016).*

Raposo G, Stoorvogel W. Extracellular vesicles: exosomes, microvesicles, and friends. J Cell Biol. Feb. 18, 2013;200(4):373-83. (Year: 2013).*

Morigi M, De Coppi P. Cell therapy for kidney injury: different options and mechanisms—mesenchymal and amniotic fluid stem cells. Nephron Exp Nephrol. 2014; 126(2):59. (Year: 2014).*

Wiklander et al. Extracellular vesicle in vivo biodistribution is determined by cell source, route of administration and targeting. J Extracell Vesicles. Apr. 20, 2015;4:26316 (Year: 2015).*

Sedrakyan S, Da Sacco S, Milanesi A, Shiri L, Petrosyan A, Varimezova R, Warburton D, Lemley KV, De Filippo RE, Perin L. Injection of amniotic fluid stem cells delays progression of renal fibrosis. J Am Soc Nephrol. Apr. 2012;23(4):661-73. (Year: 2012).*

Savickiene et al. Human Amniotic Fluid Mesenchymal Stem Cells from Second- and Third-Trimester Amniocentesis: Differentiation Potential, Molecular Signature, and Proteome Analysis. Stem Cells Int. 2015;2015:319238. (Year: 2015).*

(Continued)

*Primary Examiner* — Taeyoon Kim

(74) *Attorney, Agent, or Firm* — Schwegman, Lundberg & Woessner, P.A.

(57) ABSTRACT

Compositions and methods to treat or prevent disease or injury comprising administering an effective amount of extracellular vesicles (EVs) isolated from stem cells to a subject in need thereof.

6 Claims, 41 Drawing Sheets

Specification includes a Sequence Listing.

(56) References Cited

OTHER PUBLICATIONS

Morigi et al. Cell Therapy for Kidney Injury: Different Options and Mechanisms—Mesenchymal and Amniotic Fluid Stem Cells. Nephron Exp Nephrol 2014;126:59-63 (Year: 2014).*
Bruno et al. Role of mesenchymal stem cell-derived microvesicles in tissue repair. Pediatr Nephrol (2013) 28:2249-2254 (Year: 2013).*
What is Alport syndrome. CORE Kidney. UCLA Health. downloaded from www.uclahealth.org/programs/core-kidney/conditions-treated/alport-syndrome/what-alport-syndrome. p. 1-7 (Year: 2025).*
Huang et al. Umbilical cord-derived mesenchymal stem cells restore renal homeostasis in Alport Syndrome: Mechanistic insights and clinical translation. Journal of Advanced Research (2026), doi: https://doi.org/10.1016/j.jare.2026.04.025. Pre-proofs. p. 1-54 (Year: 2026).*
"International Application Serial No. PCT/US2017/060917, International Search Report mailed Feb. 20, 2018", 4 pgs.
"International Application Serial No. PCT/US2017/060917, Written Opinion mailed Feb. 20, 2018", 5 pgs.
Bruno, et al., "Mesenchymal Stem Cell-Derived Microvesicles Protect Against Acute Tubular Injury", Journal of the American Society of Nephrology, vol. 20, No. 5, (Apr. 23, 2009), 1053-1067.
Lee, et al., "Exosomes Derived from Mesenchymal Stem Cells Suppress Angiogenesis by Down-Regulating VEGF Expression in Breast Cancer Cells", PLoS ONE, vol. 8, Iss. 12, (Dec. 31, 2013), 1-11.
Ohno, et al., "Systemically Injected Exosomes Targeted to EGFR Deliver Antitumor MicroRNA to Breast Cancer Cells", Molecular Therapy, vol. 21, No. 1, (Oct. 2, 2012), 185-191.
Petrosan, et al., "Decellularized Renal Matrix and Regenerative Medicine of the Kidney: A Different Point of View", Tissue Engineering, vol. 22, No. 3., (Jan. 11, 2016), 183-192.
Sallustio, et al., "Potential Reparative Role of Resident Adult Renal Stem/Progenitor Cells in Acute Kidney Injury", BioResearch Open Access, vol. 4, Iss. 1, (Jul. 1, 2015), 326-333.
"International Application Serial No. PCT US2017 060917, International Preliminary Report on Patentability mailed May 23, 2019", 7 pages.
"European Application Serial No. 17869951.8, Extended European Search Report mailed Jun. 19, 2020", 7 pages.
Juan, He, "Bone marrow stem cells-derived microvesicles protect against renal injury in the mouse remnant kidney model", NEPHROLOGY, vol. 17, No. 5, (Jul. 24, 2012), pp. 493-500.
"European Application Serial No. 17869951.8, Communication Pursuant to Article 94(3) EPC mailed May 10, 2021", 5 pgs.
"European Application Serial No. 17869951.8, Response filed Jan. 7, 21 to Extended European Search Report mailed Jun. 19, 2020", 21 pgs.
"European Application Serial No. 17869951.8, Response filed Nov. 10, 2021 to Communication Pursuant to Article 94(3) EPC mailed May 10, 2021", 11 pgs.
Bruno, "Extracellular vesicles in renal tissue damage and regeneration", Eur J Pharmacol, 790, (2016), 83-91.
Camussi, Giovanni, et al., "Exosomes/microvesicles as a mechanism of cell-to-cell communication", Kidney Int, 78, (2010), 838-848.
Chiabotto, Giulia, et al., "Mesenchymal Stromal Cells Epithelial Transition Induced by Renal Tubular Cells-Derived Extracellular Vesicles", PLoS One, 11(7), (Jul. 13, 2016), 23 pgs.
Da Sacco, Stefano, et al., "A Novel Source of Cultured Podocytes", PLoS One, 8(12), (Dec. 2013), 15 pgs.
Imberti, Barbara, et al., "Potential of mesenchymal stem cells in the repair of tubular injury", Kidney International Supplements, 1, (2011), 90-93.
Keller, S, et al., "CD24 is a marker of exosomes secreted into urine and amniotic fluid", Kidney Int, 72, (2007), 1095-1102.
Lamichhane, Tek, et al., "Emerging Roles for Extracellular Vesicles in Tissue Engineering and Regenerative Medicine", Tissue Engineering: Part B, vol. 21, No. 1, (2015), 10 pgs.
Nawaz, M, et al., "Extracellular Vesicles: Evolving Factors in Stem Cell Biology", Stem Cells Int, vol. 2016, 1073140, (2016), 18 pgs.
"European Application Serial No. 17869951.8, Communication Pursuant to Article 94(3) EPC mailed May 22, 2024", 4 pgs.
"European Application Serial No. 17869951.8, Communication Pursuant to Article 94(3) EPC mailed Jun. 5, 2023", 5 pgs.
"European Application Serial No. 17869951.8, Response filed Jan. 24, 2023 to Communication Pursuant to Article 94(3) EPC mailed Sep. 26, 2022", 16 pgs.
"European Application Serial No. 17869951.8, Response filed Sep. 12, 2024 to Communication Pursuant to Article 94(3) EPC mailed May 22, 2024", 3 pgs.
"European Application Serial No. 17869951.8, Response filed Nov. 13, 2023 to Communication Pursuant to Article 94(3) EPC mailed Jun. 5, 2023", 60 pgs.

* cited by examiner

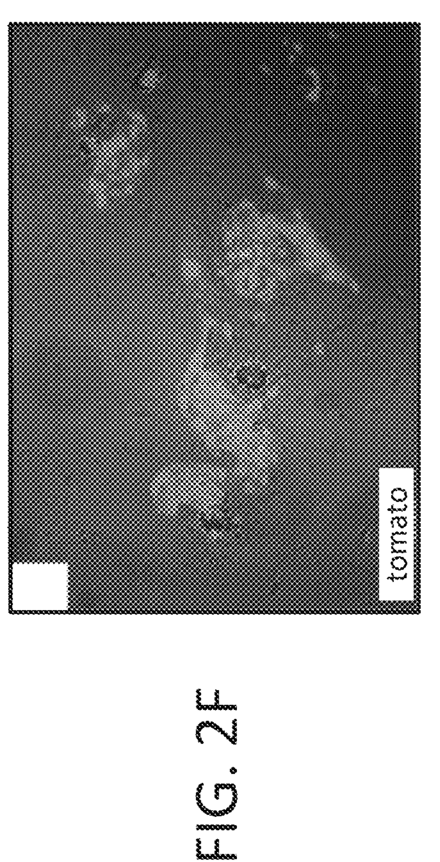
FIG. 2F
FIG. 2G
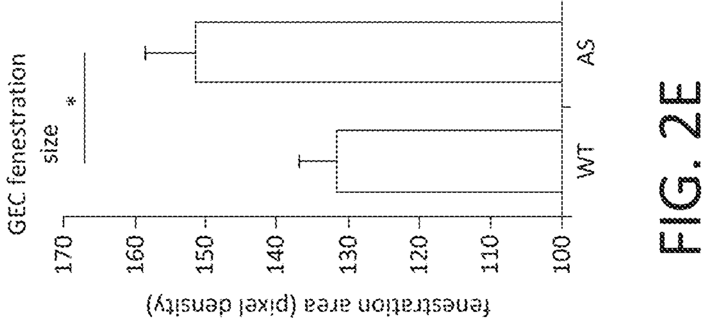
FIG. 2E

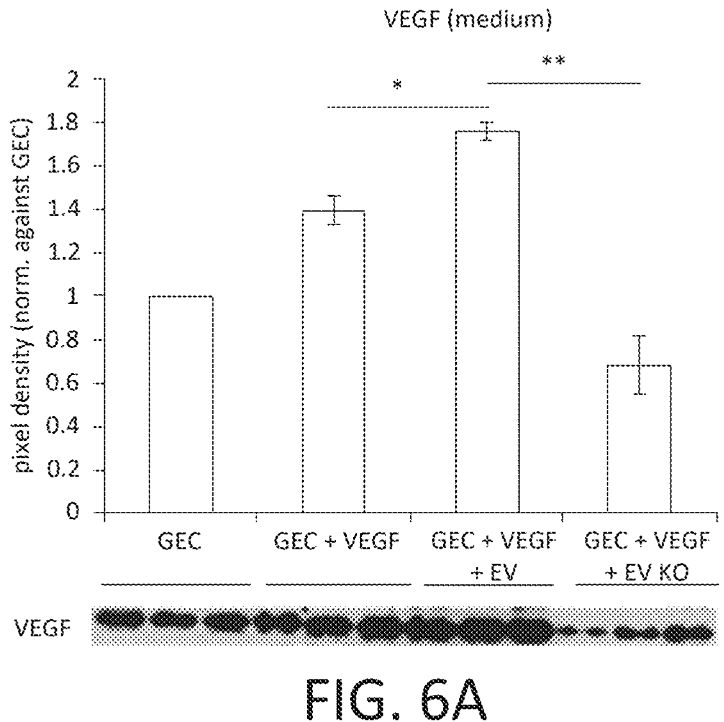
FIG. 6A
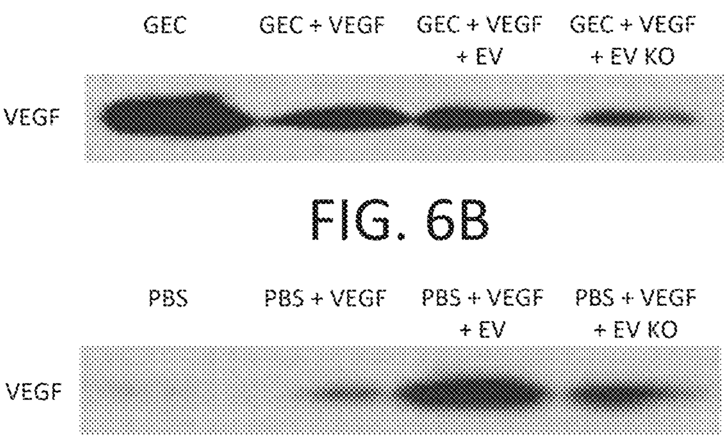
FIG. 6B
FIG. 6C

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
```

```
<223> OTHER INFORMATION: A synthetic primer

<400> SEQUENCE: 1

tcgtgtggca ggatgtgtat                                                   20


<210> SEQ ID NO 2
<211> LENGTH: 21
<212> TYPE: DNA
<213> ORGANISM: Artificial Sequence
<220> FEATURE:
<223> OTHER INFORMATION: A synthetic primer

<400> SEQUENCE: 2

acctggtgtc agtctcagag g                                                 21


<210> SEQ ID NO 3
<211> LENGTH: 21
<212> TYPE: DNA
<213> ORGANISM: Artificial Sequence
<220> FEATURE:
<223> OTHER INFORMATION: A synthetic primer

<400> SEQUENCE: 3

actcgacagg atggaaatca c                                                 21


<210> SEQ ID NO 4
<211> LENGTH: 18
<212> TYPE: DNA
<213> ORGANISM: Artificial Sequence
<220> FEATURE:
<223> OTHER INFORMATION: A synthetic primer

<400> SEQUENCE: 4

cggtgttcag cgagatcc                                                     18


<210> SEQ ID NO 5
<211> LENGTH: 20
<212> TYPE: DNA
<213> ORGANISM: Artificial Sequence
<220> FEATURE:
<223> OTHER INFORMATION: A synthetic primer

<400> SEQUENCE: 5

tcaagctgca ggtcaatgtc                                                   20


<210> SEQ ID NO 6
<211> LENGTH: 18
<212> TYPE: DNA
<213> ORGANISM: Artificial Sequence
<220> FEATURE:
<223> OTHER INFORMATION: A synthetic primer

<400> SEQUENCE: 6

ccattggcag ggtgactc                                                     18


<210> SEQ ID NO 7
<211> LENGTH: 20
<212> TYPE: DNA
<213> ORGANISM: Artificial Sequence
<220> FEATURE:
<223> OTHER INFORMATION: A synthetic primer

<400> SEQUENCE: 7

caggctgctg taacgatgaa                                                   20
```

<210> SEQ ID NO 8
<211> LENGTH: 20
<212> TYPE: DNA
<213> ORGANISM: Artificial Sequence
<220> FEATURE:
<223> OTHER INFORMATION: A synthetic primer

<400> SEQUENCE: 8
gctttggtga ggtttgatcc 20

<210> SEQ ID NO 9
<211> LENGTH: 18
<212> TYPE: DNA
<213> ORGANISM: Artificial Sequence
<220> FEATURE:
<223> OTHER INFORMATION: A synthetic primer

<400> SEQUENCE: 9
atccctcggc caacaatc 18

<210> SEQ ID NO 10
<211> LENGTH: 24
<212> TYPE: DNA
<213> ORGANISM: Artificial Sequence
<220> FEATURE:
<223> OTHER INFORMATION: A synthetic primer

<400> SEQUENCE: 10
cattctcagt gcagaagtca tacc 24

<210> SEQ ID NO 11
<211> LENGTH: 22
<212> TYPE: DNA
<213> ORGANISM: Artificial Sequence
<220> FEATURE:
<223> OTHER INFORMATION: A synthetic primer

<400> SEQUENCE: 11
cagtggtact ggcagctaga ag 22

<210> SEQ ID NO 12
<211> LENGTH: 20
<212> TYPE: DNA
<213> ORGANISM: Artificial Sequence
<220> FEATURE:
<223> OTHER INFORMATION: A synthetic primer

<400> SEQUENCE: 12
acaagcatac gggcttgttt 20

<210> SEQ ID NO 13
<211> LENGTH: 26
<212> TYPE: DNA
<213> ORGANISM: Artificial Sequence
<220> FEATURE:
<223> OTHER INFORMATION: A synthetic primer

<400> SEQUENCE: 13
cagatgaacc taggagctac cttaaa 26

<210> SEQ ID NO 14
<211> LENGTH: 20
<212> TYPE: DNA
<213> ORGANISM: Artificial Sequence
<220> FEATURE:
<223> OTHER INFORMATION: A synthetic primer

<400> SEQUENCE: 14
tctgcccttc tgtccatttc 20

<210> SEQ ID NO 15
<211> LENGTH: 24
<212> TYPE: DNA
<213> ORGANISM: Artificial Sequence
<220> FEATURE:
<223> OTHER INFORMATION: A synthetic primer

<400> SEQUENCE: 15
aaatcagtta tggttccttt ggtc 24

<210> SEQ ID NO 16
<211> LENGTH: 26
<212> TYPE: DNA
<213> ORGANISM: Artificial Sequence
<220> FEATURE:
<223> OTHER INFORMATION: A synthetic primer

<400> SEQUENCE: 16
gctctagaat taccacagtt atccaa 26

<210> SEQ ID NO 17
<211> LENGTH: 22
<212> TYPE: RNA
<213> ORGANISM: Artificial Sequence
<220> FEATURE:
<223> OTHER INFORMATION: A synthetic primer

<400> SEQUENCE: 17
uaccuguaga accgaauuug ug 22

<210> SEQ ID NO 18
<211> LENGTH: 22
<212> TYPE: RNA
<213> ORGANISM: Artificial Sequence
<220> FEATURE:
<223> OTHER INFORMATION: A synthetic primer

<400> SEQUENCE: 18
ucguaccgug aguaauaaug cg 22

<210> SEQ ID NO 19
<211> LENGTH: 22
<212> TYPE: RNA
<213> ORGANISM: Artificial Sequence
<220> FEATURE:
<223> OTHER INFORMATION: A synthetic primer

<400> SEQUENCE: 19
uaacagucua cagccauggu cg 22

<210> SEQ ID NO 20
<211> LENGTH: 22
<212> TYPE: RNA
<213> ORGANISM: Artificial Sequence
<220> FEATURE:
<223> OTHER INFORMATION: A synthetic primer

<400> SEQUENCE: 20
cugugcgugu gacagcggcu ga 22

<210> SEQ ID NO 21
<211> LENGTH: 22

<212> TYPE: RNA
<213> ORGANISM: Artificial Sequence
<220> FEATURE:
<223> OTHER INFORMATION: A synthetic primer

<400> SEQUENCE: 21
uagcagcaca uaaugguuug ug 22

<210> SEQ ID NO 22
<211> LENGTH: 22
<212> TYPE: RNA
<213> ORGANISM: Artificial Sequence
<220> FEATURE:
<223> OTHER INFORMATION: A synthetic primer

<400> SEQUENCE: 22
uagcagcacg uaaauauugg cg 22

<210> SEQ ID NO 23
<211> LENGTH: 23
<212> TYPE: RNA
<213> ORGANISM: Artificial Sequence
<220> FEATURE:
<223> OTHER INFORMATION: A synthetic primer

<400> SEQUENCE: 23
caaagugcug uucgugcagg uag 23

<210> SEQ ID NO 24
<211> LENGTH: 22
<212> TYPE: RNA
<213> ORGANISM: Artificial Sequence
<220> FEATURE:
<223> OTHER INFORMATION: A synthetic primer

<400> SEQUENCE: 24
uaauacugcc ugguaaugau ga 22

<210> SEQ ID NO 25
<211> LENGTH: 22
<212> TYPE: RNA
<213> ORGANISM: Artificial Sequence
<220> FEATURE:
<223> OTHER INFORMATION: A synthetic primer

<400> SEQUENCE: 25
cagcagcaau ucauguuuug ga 22

<210> SEQ ID NO 26
<211> LENGTH: 22
<212> TYPE: RNA
<213> ORGANISM: Artificial Sequence
<220> FEATURE:
<223> OTHER INFORMATION: A synthetic primer

<400> SEQUENCE: 26
uagcuuauca gacugauguu ga 22

<210> SEQ ID NO 27
<211> LENGTH: 21
<212> TYPE: RNA
<213> ORGANISM: Artificial Sequence
<220> FEATURE:
<223> OTHER INFORMATION: A synthetic primer

<400> SEQUENCE: 27

-continued

```
aucacauugc cagggauuuc c                                         21


<210> SEQ ID NO 28
<211> LENGTH: 21
<212> TYPE: RNA
<213> ORGANISM: Artificial Sequence
<220> FEATURE:
<223> OTHER INFORMATION: A synthetic primer

<400> SEQUENCE: 28

uucacagugg cuaaguuccg c                                         21


<210> SEQ ID NO 29
<211> LENGTH: 23
<212> TYPE: RNA
<213> ORGANISM: Artificial Sequence
<220> FEATURE:
<223> OTHER INFORMATION: A synthetic primer

<400> SEQUENCE: 29

guccaguuuu cccaggaauc ccu                                       23


<210> SEQ ID NO 30
<211> LENGTH: 21
<212> TYPE: RNA
<213> ORGANISM: Artificial Sequence
<220> FEATURE:
<223> OTHER INFORMATION: A synthetic primer

<400> SEQUENCE: 30

uugugcuuga ucuaaccaug u                                         21


<210> SEQ ID NO 31
<211> LENGTH: 23
<212> TYPE: RNA
<213> ORGANISM: Artificial Sequence
<220> FEATURE:
<223> OTHER INFORMATION: A synthetic primer

<400> SEQUENCE: 31

agcuacauug ucugcugggu uuc                                       23
```

EXTRACELLULAR VESICLES FROM STEM CELLS TO TREAT AND/OR PREVENT DISEASE

PRIORITY

This application is a U.S. national stage application filed under 35 U.S.C. § 371 from International Application Serial No. PCT/US2017/060917, filed on Nov. 9, 2017, and published as WO 2018/089672 on May 17, 2018, which claims the benefit of priority from U.S. Provisional Patent Application Ser. No. 62/419,812, filed on Nov. 9, 2016, which applications are herein incorporated by reference in their entireties.

BACKGROUND

It was previously demonstrated that stem cells derived from amniotic fluid (AFSC) are renoprotective and significantly delayed disease progression in a mouse model of Alport Syndrome (AS, where a mutation in any of the collIV$\alpha$3,$\alpha$4,$\alpha$5 genes results in the disruption of the glomerular basement membrane (GBM), podocyte effacement and renal failure) via preservation of podocyte number and maintenance of glomerular function (10).

SUMMARY

Injection of amniotic fluid stem cells (AFSC) delays the course of progression of renal fibrosis in animals with Alport Syndrome, enhancing kidney function and improving survival. The mechanisms responsible for these protective outcomes are still largely unknown. It is described herein that vascular endothelial growth factor (VEGF) signaling within the glomeruli of Alport mice is strongly elevated early on in disease causing glomerular endothelial cell damage. Intra-ventricularly injected AFSC that homed within the glomeruli showed strong modulation of the VEGF activity particularly in glomerular endothelial cells. To investigate this phenomenon, it was hypothesized that extracellular vesicles produced by the AFSC could be responsible for the observed renoprotection. AFSC derived extracellular vesicles presented exosomal and stem cell makers on their surface membrane, including VEGFR1 and VEGFR2, and contained angiomodulatory microRNAs. Extracellular vesicles were able to modulate VEGF in glomerular endothelial cells by effectively trapping the excess VEGF through VEGFR1-binding preventing cellular damage. In contrast, VEGFR1/sFlt1 knockout extracellular vesicles failed to show similar protection, thus indicating that VEGF trapping is a mechanism for AFSC mediated renoprotection in mice. Taken together, the findings demonstrate the ability of AFSC to ameliorate renal damage and establish that extracellular vesicles secreted by AFSC target a specific signaling pathway within the glomerulus, thus representing a novel glomerulus-specific targeted intervention.

One embodiment provides a method to treat or prevent kidney disease or injury comprising administering an effective amount of extracellular vesicles (EVs) isolated from stem cells to a subject in need thereof. Another embodiment provides a method to treat or prevent pre-eclampsia comprising administering an effective amount of extracellular vesicles isolated from stem cells to a subject in need thereof. One embodiment provides a method to decrease tumor growth, decrease dysfunctional neovascularization caused by VEGF signaling and/or treat a disease characterized by altered VEGF homeostasis comprising administering an effective amount of extracellular vesicles isolated from stem cells to a subject in need thereof. Another embodiment provides a method to capture VEGF, TGFβ and/or ang II molecules in vitro or in vivo comprising contacting a biological sample with extracellular vesicles isolated from stem cells.

In one embodiment the kidney disease is chronic kidney disease. In another embodiment the kidney disease results in Aplort syndrome. In one embodiment, the stem cells are embryonic stem cells, adult stem cells or induced pluripotent stem cells. In one embodiment the stem cells are amniotic fluid stem cells (AFSCs). In one embodiment the EVs are administered by local or systemic injection. In one embodiment, the injury is a result of physical trauma.

One embodiment provides a composition comprising EVs from amniotic fluid stem cells and a physiologically acceptable carrier.

BRIEF DESCRIPTION OF FIGURES

FIGS. 2A-M. GEC damage in Alport mice. Alport mice showed GEC damage during early stage of disease (AE). Representative transmission electron microscopy images showing characteristic thinning and splitting of the GBM in Alport mice (arrow, A, 28,000×), enlarged endothelial fenestrations and ruptured endothelial layer (arrow, B, 28,000×) when compared to their littermate WT mice (C-D, 28,000×). GEC fenestrations were enlarged in Alport mice at 3 months of age when compared to the WT mice as shown by the graph in E. Fenestration size was measured by ImageJ in 20 TEM images from 3 samples for each group. VEGF signaling changes in GEC were studied using tdtomato-labeled GEC (tdT GEC) isolated by FACS from Alport-Tek$^{tdT}$ glomeruli (F, 10×). tdT signal (red) is strongly present in all cells as shown in G (10×, two passages in culture). Higher mRNA expression for CD31 (H) was evident in tdT-GEC, while neg-tdT-GEC expressed higher PDGFRB (1) and WT1 (J). Alport-Tek$^{tdT}$ GEC had higher mRNA for VEGFR2 (K) and AKT (L) expression than the WT-Tek$^{tdT}$ GEC at 3 months of age. M. Graph representing immunoblot data of increased pVEGFR2 (230 kDa) in Alport-Tek$^{tdT}$ GEC compared to their WT littermates at 3 months of age. Immunoblots were quantified by densitometry (all measurements were normalized against their corresponding housekeeping gene, β-actin, 42 kDa). Values are presented as mean #SEM (*p<0.05).

Figure 1A:
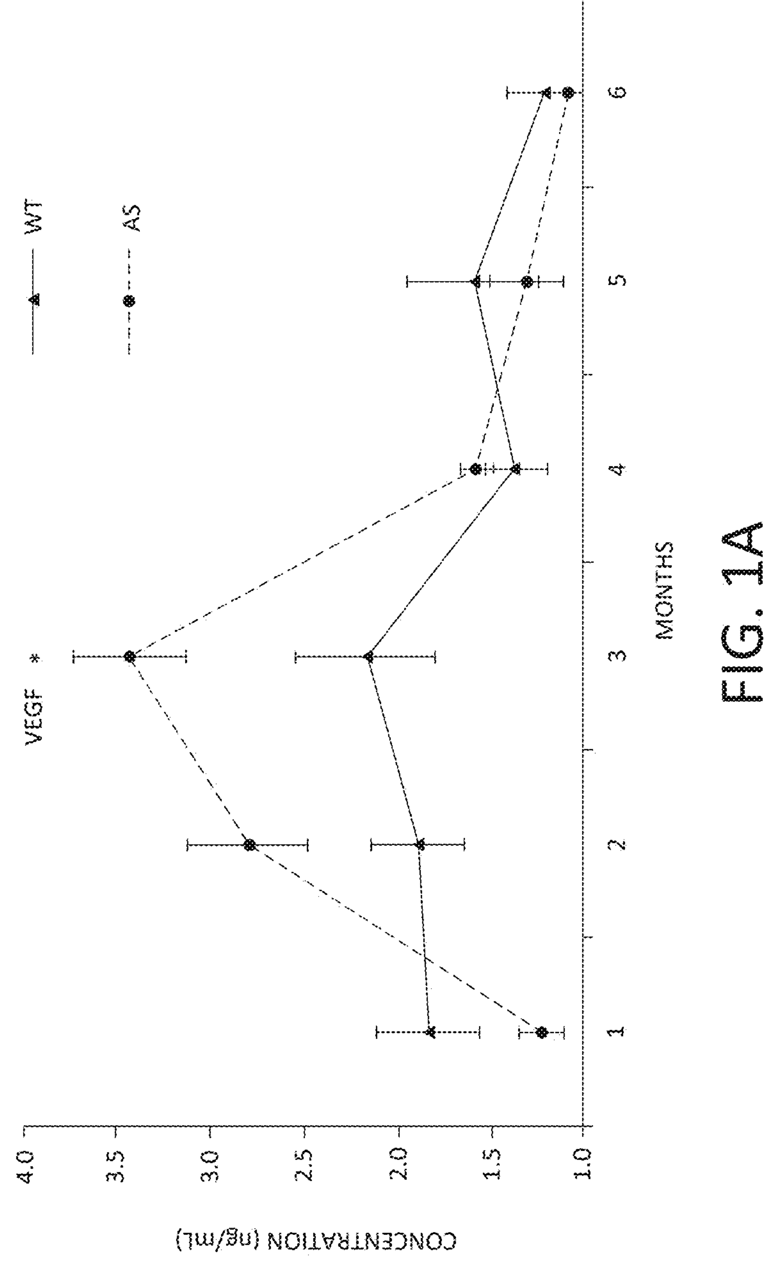
FIGS. 1A-H. Evaluation of VEGF, pVEGFR2, VEGFR1 and sFlt1 expression within Alport glomeruli during disease progression. Changes in VEGF signaling activity were evaluated in glomeruli isolated from kidneys of WT and Alport mice over the course of disease progression from 1 to 6 months of age by ELISA, immunohistochemistry and Western Blot. As shown in the graph, VEGF increased gradually during the early phase of disease peaking at 3 months and dropped thereafter (A). VEGF staining at 3 months confirmed the presence of elevated VEGF expression (green) in Alport glomeruli (B, 40×) as compared against WT controls (C, 40×). Nuclear staining with DAPI (blue). Graphs representing immunoblot data of increased pVEGFR2 (D, 230 kDa) and decreased VEGFR1 expression (E, 151 kDa) in glomeruli of Alport mice compared to their WT littermates at 3 months of age. Immunoblots were quantified by densitometry (all measurements were normalized against their corresponding housekeeping gene, β-actin, 42 kDa). sFlt1 expression measured by Elisa decreased in advanced Alport glomeruli as compared to time-matched siblings (F). Graphs representing immunoblot data for pVEGFR2 (G) and VEGFR1 (H) at 6 months of age, showing the decrease of both proteins in Alport glomeruli as compared to their time-matched WT controls. Immunoblots were quantified by densitometry (all measurements were normalized against their corresponding housekeeping gene, β-actin, 42 kDa). All values are presented as mean #SEM (*$p<0.05$).

FIGS. SA-F. Generation of AFSC/EV$^{Flt1-/-}$ and VEGFR2 and VEGFR1 modulation by AFSC-EVs in GEC. A. Different viable clones obtained from AFSC transduced with Flt1 shRNA lentiviral particles where analyzed by qPCR for Flt1 expression after puromycin selection. AFSC were transduced with different titrations of viral particles (5, 10, 20 MOI) to obtain the best transduction efficiency. As shown, resulting puromycin-resistant clones have varying levels of Flt1 expression due to the random integration of the lentiviral construct into the genome of the cells. Clone A6 (first column) was selected as the most efficient. B. Relative gene expression of Flt1 in non-transduced AFSC compared to Fit1 KO AFSC (clone A6) showing 90% reduction. VEGFR1 protein (151 KDa) expression was quantified by Western Blot analysis in cell lysates of AFSC and KO AFSC (clone A6) (C) and EVs isolated from both cell populations (D) showing respectively 50% and 60% reduction. All measurements were normalized against their corresponding housekeeping gene, β-actin, 42 kDa. E-F. Graphs showing differential expression of pVEGFR2 (E, 230 KDa) and VEGFR1 (F, 151 KDa) in GEC (basal condition, control), GEC stimulated with VEGF (100 ng/ml) and treated with EVs and KO EVs for 24 hr. Both pVEGFR2 and VEGFR1 were restored to basal level in the presence of normal EVs, but not in the presence of EVFIt1−/−. Data from 3 samples per group were quantified (measurements were normalized against their corresponding housekeeping gene, β-actin, 42 KDa; Western Blot bands are presented below the graphs. Values are presented as mean±SEM (*p<0.05).

FIGS. 6A-C. VEGF modulation by AFSC-EVs in GEC and AFSC-EV binding. A. Graph showing level of VEGF (24 KDa, monomer) within the media collected from GEC (basal condition, control), GEC stimulated with VEGF (100 ng/ml) and treated with EVs and KO EVs for 24 hr. VEGF level was higher in GEC stimulated with normal EVs compared to GEC stimulated with EV$^{Flt-/-}$. Data from 3 samples per group were quantified (measurements were normalized against VEGF basal level (in GEC) since Western Blot was performed in collected media; Western Blot bands are presented below the graph). Values are presented as mean±SEM (*p<0.05). B. Representative immunoblot of VEGF after co-immunoprecipitation with VEGFR1 on the supernatant collected from experimental groups described in A, showing the inefficiency of the EV$^{Flt-/-}$ to trap VEGF when compared to that of normal EVs. C. Representative immunoblot of VEGF, after co-immunoprecipitation with VEGFR1 on samples of PBS solution containing high VEGF dose (100 ng/ml) and treated with EVs and KO EVs for 24 hr further confirming the inability of the EV$^{Flt-/-}$ to effectively trap VEGF compared to normal EVs. The weak band detected in the PBS/VEGF only group represent a VEGF carryover due to incomplete removal of VEGF during the washing steps.

FIGS. 7A-H. Characterization of GEC from WT-Tekut mice. Representative pictures showing co-localization of tomato signal (red) with CD31 (green) in glomeruli of WTTe$^{tdT}$ mice (A-D). Expressions of CD31 and tdT are predominantly co-localized within the glomeruli of Tek$^{tdT}$ mice (B, 10×; D, 40×) while no co-expression is present in WT mice (A, 10×; C, 40×). Nuclear staining with DAPI (blue). E. Representative histogram of the tdT signal analyzed by flow cytometry showing the presence of two distinct tdT positive cell populations and their percent distributions (neg-tdT cells: 54.6%, dim tdT: 11.0% and bright tdT: 43.3%). Graphs comparing the expression of endothelial genes in the dim tdT cells against the neg-tdT cells by RT-PCR for CD31 (F), PDGFRβ(G), and WT1 (H) respectively. These data show lack of strong expression of endothelial marker CD31 in the dim tdT cells.

FIGS. 8A-F. AFSC homing. Representative bright field image of AFSC in culture before being tagged with a fluorescent dye (Q-dot) (A, 10×) and after tagging for in vivo detection (B, 10×). AFSC (red) homed predominantly within glomeruli of AS mice, detected by fluorescence microscopy at 5 days (C-D) and by FACS (5 days and 10 weeks, E-F) post injection. AFSC (magenta) were found localized in close association with the endothelial cells (VE-Cadherin, green) as opposed to podocytes (CD2AP, red) within the glomerulus (D, 40×). Nuclear staining with DAPI (blue). Representative scatter graphs from flowcytometric analysis of the distribution of the Qdot positive AFSC within the different organs at 5 days (E) and 10 weeks (F) post injection.

FIGS. 9A-K. AFSC rescue GEC damage induced by VEGF overexpression. GEC ($2.0\times10^4$ cell/cm$^2$) were exposed to 100 ng/ml recombinant VEGF for 24 hrs to simulate peak VEGF conditions observed in Alport mice at 3 months of age. GEC damage and disruption of VEGF signaling and effects of AFSC were assessed by immunoblotting and immunohistochemistry (A-F). VEGF overstimulation caused increased expression of VEGF (43 KDa, dimer) and pVEGFR2 (230 KDa), whereas VEGFR1 (151 KDa) remained unchanged (A-B). Immunoblot measurements were normalized against their corresponding housekeeping gene, β-actin, 42 KDa. Representative immunohistochemistry images showed increased CD31 staining (C-D, 10×, green) and disrupted pattern for VE-Cadherin (E-F, 10×, green) in GEC exposed to VEGF as compared with non-stimulated controls. Nuclear staining with DAPI (red). Representative bright field images of GEC with and without exposure to VEGF and after treatment with AFSC (G-I, 10×). These observations showed disrupted GEC morphology with VEGF overstimulation (H) compared to control non-stimulated GEC (G). GEC co-cultured with AFSC (at 1:1 ratio on transwell) on the other hand improved cell morphology (I). J. Graph representing the GEC counts after 24 hrs of VEGF overstimulation resulted in reduced cell counts that were ameliorated with AFSC treatment. K. PCR-array demonstrating the modulation of specific endothelial gene, including VEGF, by AFSC.

FIGS. 10A-I. AFSC-EV miRNA characterization and AFSC-EV uptake by GEC. A. Fold change analysis of miRNAs expression in AFSC-derived EVs. The snoRNA RNU6b was used as normalizing reference control. Fold change in miRNA expression was calculated as $2^{-\Delta Ct}$ using the geometric mean in Ct values as normalizer. Data are represented as the mean±SD of 4 different experiments. In order to demonstrate uptake of AFSC-derived EVs by GEC, GEC were incubated with AFSC-labeled-EVs for 16 hours. B-I. Representative images (bright field and fluorescence) of GEC in culture in the presence of GFPEVs (green) derived from AFSCGFP and also labeled with CM-Dil (red) before exposure, immediately after exposure (0 hrs) and 16 hrs later (40×). As evident in the merged picture (1), double labeled EVs are present within the perinuclear of GEC.

DETAILED DESCRIPTION

Over the past decade investigations into the mechanisms of stem cell mediated recovery of kidney injury has elucidated that stem cells transiently home into the site of injury without replacing renal cells. Instead they seem to mitigate renal damage through paracrine secretion of "healing molecules." Recently, it was shown that extracellular vesicles (EV) secreted by stem cells can modulate molecular signaling stimulating endogenous cell repair. Described herein is the evaluation of the potential of AFSC and their secreted EVs of modulating VEGF signaling in glomerular endothelial cells.

VEGF is a potent angiogenic factor expressed in the glomerulus of developing and mature kidneys and the cross-talk between podocytes and endothelial cells through VEGF plays a role in the maintenance of glomerular capillary networks. Alteration of VEGF signaling has been implicated in a number of chronic kidney diseases (including diabetes nephropathy and IgA nephropathy). Even if accumulation of VEGF was reported in Alport human kidneys, the impact of VEGF changes and its possible correlation with endothelial damage have not been studied. Moreover, whether alterations in VEGFR1 and its soluble form sFlt1 (which are well known as negative regulators of endogenous levels of VEGF), contribute to the pathogenesis of glomerular endothelium is not fully understood.

For the first time the role of VEGF/VEGFRs signaling in Alport disease has been identified. The data demonstrate that VEGF singling is altered during the early stage of the disease when proteinuria has not yet reached high levels, thus indicating that VEGF is implicated on the progressive pathogenesis of Alport Syndrome by initiating glomerular endothelial damage. It is demonstrated herein the ability of AFSC, as well as of their secreted EVs, to specifically target the VEGF signaling pathway in glomerular endothelial cells. VEGFR1 expressed by the EVs was found to be involved in trapping the excess local VEGF, thus ultimately modulating VEGFR activity and restoring glomerular endothelial biology.

Thus, provided herein is a novel approach to mitigate the deleterious effects of VEGF signaling within a specific renal compartment: the glomerulus, thus offering a new potential glomerulus-specific targeted intervention. Provided herein is also a novel discovery in cell technology because the use of stem cell derived products, like EVs, has the potential to be generalized beyond renal biology. VEGF signaling is altered in many different diseases, ranging from preeclampsia to promoting dysfunctional neovascularization or accelerating tumor growth, therefore the delivery of EVs by stem cells (including AFSC) can represent a tool for specifically targeting VEGF in the organ of interest, thus favoring a local therapeutic action on VEGF signaling where it is needed.

Definitions

Embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In addition, it is to be understood that the phraseology or terminology employed herein, and not otherwise defined, is for the purpose of description only and not of limitation.

All percentages and ratios used herein are by weight of the total composition and all measurements made are at 25° C., unless otherwise designated.

All numeric ranges are inclusive of narrower ranges; delineated upper and lower range limits are interchangeable to create further ranges not explicitly delineated. The number of significant digits conveys neither limitation on the indicated amounts nor on the accuracy of the measurements.

In this document, the terms "a" or "an" are used to include one or more than one and the term "or" is used to refer to a nonexclusive "or" unless otherwise indicated. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "isolated" or an "enriched population" refers to a cell or cells which are not associated with one or more cells or one or more cellular components that are associated with the cell or cells in vivo.

A "subject" is a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, orangutan) rat, sheep, goat, cow and bird.

An "effective amount" generally means an amount which provides the desired local or systemic effect and/or performance, particularly for treating a condition of interest. For example, an effective dose is an amount sufficient to affect a beneficial or desired clinical result. Said dose could be administered in one or more administrations and could include any preselected amount of cells. The precise determination of what would be considered an effective dose may be based on factors individual to each subject, including their size, age, size of the damage, and amount of time since the damage occurred or the disease began. One skilled in the art, specifically a physician, would be able to determine the number of cells that would constitute an effective dose.

"Expansion" refers to the propagation of cells without differentiation.

"Renal function" generally refers to a physiological property of the kidney, such as the ability to retain protein thereby preventing proteinuria (e.g., urinary creatinine, the excretion of protein in an amount greater than about 0.15 g/24 hours). Renal function can be assessed, for example, by glomerular filtration rate (e.g., creatinine clearance), excretion of protein in urine, blood urea nitrogen, serum or plasma creatinine, or any combination thereof.

"Podocytes" are specialized, highly differentiated pericyte-like cells of the visceral epithelium in the kidneys. Podocytes form a crucial component of the glomerular filtration barrier, contributing size and charge selectivity and maintaining a massive filtration surface. "Pedicels" (or "foot processes") extend from the podocyte. These delicate foot processes cover the exterior basement membrane surface of the glomerular capillary. Adjacent podocytes interdigitate to cover the basal lamina which is intimately associated with the glomerular capillaries; however, gaps or thin filtration slits remain. When podocytes contract, they cause closure of the filtration slits. This decreases the glomerular filtration rate (GFR) by reducing the surface area available for filtration. Furthermore, podocytes are known to synthesize matrix molecules to the glomerular basement membrane (GBM), including type IV collagen, laminin, entactin, and agrin. Podocyte injury or loss leads to proteinuria, where large amounts of protein are lost from the blood. Moreover, loss of podocytes is a hallmark of diabetic and nondiabetic progressive chronic kidney disease (CKD).

"Self-renewal" refers to the ability to produce replicate daughter cells having differentiation potential that is identical to those from which they arose. A similar term used in this context is "proliferation."

As used herein, "treat," "treating" or "treatment" includes treating, reversing, preventing, ameliorating, or inhibiting an injury or disease-related condition or a symptom of an injury or disease-related condition.

"Co-administer" can include simultaneous and/or sequential administration of two or more agents/cell types.

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods.

The terms "comprises," "comprising," and the like can have the meaning ascribed to them in U.S. Patent Law and can mean "includes," "including" and the like. As used herein, "including" or "includes" or the like means including, without limitation.

Isolation and Characterization of EVs from Stem Cells

Stem cells are undifferentiated biological cells (with various levels of potency—e.g., totipotent, pluripotent, multipotent, oligopotent, unipotent) that can differentiate into specialized cells and can divide (through mitosis) to produce more stem cells. They are found in multicellular organisms. In mammals, there are two broad types of stem cells: embryonic stem cells, which are isolated from the inner cell mass of blastocysts, and adult stem cells, which are found in various tissues. There are also induced pluripotent stem cells. In adult organisms, stem cells and progenitor cells act as a repair system for the body, replenishing adult tissues. In a developing embryo, stem cells can differentiate into all the specialized cells—ectoderm, endoderm and mesoderm—but also maintain the normal turnover of regenerative organs, such as blood, skin, or intestinal tissues. Stem cells can be used in the methods of the invention to, for example, generate and isolate extracellular vesicles (EVs).

Amniotic fluid stem cells (AFSC) are renoprotective. AFSC secrete extracellular vesicles (EVs) that can modulate glomerular signaling. Specifically herein, EVs were characterized for their content and specific micro-RNA (miRs) were identified that modulate VEGF signaling within the glomerulus of mice affected by glomerular disease (Alport mice) and placenta. EVs from AFSCs have a protective role in diseases characterized by altered VEGF homeostasis in glomeruli, such as Alport syndrome or pre-eclampsia.

Thus, EVs can be delivered to patients instead of stem cells. EVs are not immunogenic. EVs can be an off the shelf product that can be delivered for the treatment of patients affected by chronic kidney disease (CKD) or preeclampsia. In addition, EVs can represent a model of biomarker identification in CKD, an unmet medical need.

EVs can be isolated and characterized, both in vitro and in vivo, by methods available to an art worker.

Uses for EVs

EVs can be delivered to patients instead of stem cells. EVs are not immunogenic and can be very well tolerated by patients. They are target specific and can be modified to target specific pathways and cells. EVs can be administered for the treatment of patients affected by, for example, kidney disease CKD or preeclampsia.

Disease states characterized by loss of kidney mass and/or function, and that could benefit from EVs and methods of the invention include, but are not limited to, kidney disease or injury. For example, one therapeutic use of the EVs of the invention is for treating a subject with a renal disease, promoting growth of new tissue in a subject, or promoting survival of damaged tissue in a subject. Therapeutic use of the EVs of the invention includes treatment of kidney diseases. The kidney disease can be, for example, a result or a consequence of any change, damage, or trauma to the glomerulus, tubules or interstitial tissue in either the renal cortex or renal medulla of the kidney. The kidney disease can be acute or chronic.

A subject may be regarded as being in, or at risk of, chronic renal failure, or at risk of needing renal replacement therapy, if that subject has already been diagnosed as afflicted with, or would be regarded as being afflicted with, a condition which typically leads to progressive loss of renal function associated with progressive loss of functioning nephron units. Such conditions or causes include, but are not limited to, chronic renal failure, end-stage renal disease, hypertensive nephrosclerosis, hereditary nephritis, renal dysplasia, diabetes, sepsis, dehydration, medication (e.g., excessive water loss due to diuretic intake, NSAIDs including ibuprofen and naproxen, antibiotics like aminoglycosides (gentamicin, tobramycin,) lithium, and iodine-containing medications), loss of blood supply due to obstruction of the renal artery or vein, rhabdomyolysis, multiple myeloma, systemic lupus erthematosus, obstruction of bladder, high blood pressure, prostatic hypertrophy or prostate cancer, renal cancer, tumors, kidney stones and the like.

In some embodiments, the kidney disease is a progressive kidney disease. In some embodiments, the kidney disease is a progressive glomerular kidney disease. Progressive glomerular kidney diseases that are particularly suitable for treatment by the methods described herein include, for example, diabetic nephropathy (e.g., as a consequence of Type I or Type II diabetes or systemic lupus), primary glomerulonephritis (e.g., membranous nephropathy, focal segmental glomerulosclerosis, membranoproliferative glomerulonephritis, diffuse proliferative glomerulonephritis, membranous focal segmental glomerulosclerosis, mild glomerular lesions, mesangial proliferative glomerulonephritis including IgA nephropathy, intraductal proliferative glomerulonephritis, mesangial capillary glomerulonephritis, high-density precipitation glomerulonephritis, crescentic glomerulonephritis including extratubal glomerulonephritis, and sclerosing glomerulonephritis) and secondary glomerulonephritis (e.g., ischemic nephropathy, glomerular disease based on systematic disease including lupus nephritis and Goodpasture syndrome, glomerular diseases based on vascular disease including glomerular thrombosis, glomerular disease based on metabolic diseases including diabetic nephropathy and amyloidosis, hereditary renal lesions including Alport's syndrome, and transplanted glomerular lesions). Further kidney diseases include Finnish-type nephrosis, ischemia-reperfusion injury, congenital nephrotic syndrome, pyelonephritis, interstitial nephritis, acute tubular necrosis, pharmaceutical drug or toxicant renal disorder, acute nephritis syndrome, rapidly progressive glomerulonephritis syndrome, relapsing and continuous hematuria, and chronic nephritis syndrome.

Treatment/Administration of

More than 31 million people suffer from CKD in USA. The cost for current treatments is over $70,000 per patient every year. Currently, the only treatments for kidney disease are medications and dialysis, until a kidney transplantation is required.

EVs can be obtained from numerous stem cell types, such as those disclosed above. For the purposes described herein, either autologous, allogeneic or xenogeneic EVs obtained from stem cells such as such as amniotic fluid derived renal progenitor cells can be administered to a subject, genetically altered or unaltered, by direct injection to a tissue site, systemically, on or around the surface of an acceptable matrix, encapsulated or in combination with a pharmaceutically acceptable carrier.

EVs of the invention can be administered to a subject by a variety of methods known in the art. EVs of the invention can be administered to a subject by localized or systemic injection. EVs can also be administered by surgical intramyocardial injection, transendocardial injection, intracoronary injection, transvascular injection, intramuscular injection, and intravenous injection. EVs may be administered within or in proximity to the site requiring new cells, mass, or enhanced function alternatively they can be administered at a remote location.

In one embodiment, a EV suspension is drawn up into a syringe and administered to a subject. Multiple injections may be made using this procedure. The use of such a suspension procedure provides many advantages. For example, these methods direct EVs to any predetermined site and are relatively non-traumatic.

Typically, the number of EVs administered into a subject will be a "therapeutically effective amount." As used herein, a "therapeutically effective amount" refers to the number of administered EVs that are required to effect treatment of the particular injury, or disease for which treatment is sought. For example, where the treatment is for tissue injury, administered of a therapeutically effective amount of EVs will typically produce a reduction in the amount and/or severity of the symptoms associated with the injury. Persons of skill in the art will understand how to determine proper EV dosages.

Exogenous factors (e.g., cytokines, differentiation factors and other factors) can be administered prior to, after or concomitantly with the EVs. For example, a form of concomitant administration would comprise combining a factor of interest in the culture media and/or pharmaceutically acceptable carrier prior to administration. Doses for administrations are variable, may include an initial administration followed by subsequent administrations; but nonetheless, can be ascertained by the skilled artisan, from this disclosure, the documents cited herein, and the knowledge in the art.

A parameter involved in the therapeutic use of EVs is the quantity of EVs necessary to achieve an optimal effect. Different scenarios may require optimization of the amount of EVs injected into a tissue of interest. For example, the quantity of EVs to be administered will vary for the subject being treated. In one embodiment, between $10^4$ to $10^8$, including $10^5$ to $10^7$, and including $3\times10^7$ cells and optionally, 50 to 500 μg/kg per day of a cytokine can be administered to a human subject. However, the precise determination of what would be considered an effective dose may be based on factors individual to each patient, including their size, age, size tissue damage, and amount of time since the damage occurred. Therefore, dosages can be readily ascertained by those skilled in the art from this disclosure and the knowledge in the art.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired. Examples of compositions comprising progenitor cells of the invention include liquid preparations for administration, including suspensions; and, preparations for intramuscular or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, which is incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (e.g., purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes.

Viscosity of the compositions, if desired, can be maintained at the selected level using a pharmaceutically acceptable thickening agent. Methylcellulose is readily and economically available and is easy to work with. Other suitable thickening agents include, for example, xanthan gum, carboxymethyl cellulose, hydroxypropyl cellulose, carbomer, and the like. The concentration of the thickener will depend upon the agent selected. The point is to use an amount, which will achieve the selected viscosity. Viscous compositions are normally prepared from solutions by the addition of such thickening agents.

A pharmaceutically acceptable preservative or stabilizer can be employed to increase the life of the compositions.

Those skilled in the art will recognize that the components of the compositions should be selected to be chemically inert. This will present no problem to those skilled in chemical and pharmaceutical principles, or problems can be readily avoided by reference to standard texts or by simple experiments (not involving undue experimentation), from this disclosure and the documents cited herein.

Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable and may include an initial administration followed by subsequent administrations; but nonetheless, can be ascertained by the skilled artisan, from this disclosure, the documents cited herein, and the knowledge in the art.

The following example is intended to further illustrate certain embodiments of the invention and is not intended to limit the scope of the invention in any way.

Example

Introduction

The complex local autocrine/paracrine signaling between podocytes and glomerular endothelial cells (GEC) is involved in the homeostatic balance of the filtration barrier (1). In particular, podocytes secrete various factors that act directly on the glomerular endothelium (2-3). In recent years multiple studies have demonstrated that vascular endothelial growth factor (VEGF) signaling plays a key role in the development and maintenance of glomerular capillary network and endothelial permeability (4-5). An angiogenic imbalance between VEGF (specifically VEGF-A), VEGF receptor 2 (VEGFR2) and the soluble vascular endothelial growth factor receptor 1 (sFlt1, a truncated variant of the VEGF receptor 1, VEGFR1) has been reported in many diseases, including kidney disease where modulation of VEGF signaling correlates with impaired endothelial fenestrations, endothelial dysfunction and increased proteinuria (5-9). Despite the existence of literature elucidating the pivotal importance of VEGF signaling dysregulation in a wide range of renal diseases, the significance of VEGF/VEGFRs/sFlt1 modulation within the local glomerular environment, its contribution to GEC damage and progression of chronic kidney disease (CKD) is still not clearly understood.

It was previously demonstrated that stem cells derived from amniotic fluid (AFSC) are renoprotective and significantly delayed disease progression in a mouse model of Alport Syndrome (AS, where a mutation in any of the colIV$\alpha$3,$\beta$4, $\alpha$5 genes results in the disruption of the glomerular basement membrane (GBM), podocyte effacement and renal failure) via preservation of podocyte number and maintenance of glomerular function (10). The renoprotection by AFSC could possibly be ascribed to their ability to secrete various trophic mediators able to stimulate endogenous glomerular repair mechanisms. In this context, stem cell derived extracellular vesicles (EVs), which are important cell-to-cell communication vehicles (11) are suggested to be involved in tissue protective mechanisms (12-13). At present, the mechanism(s) responsible for the therapeutic effect of AFSC on GEC damage and in particular their possible modulation of the VEGF pathway within the glomerulus has not yet been investigated.

In the in the instant example, an imbalanced VEGF signaling activity within the Alport glomeruli was found, particularly during the initiation phase of the disease. Injected AFSC that lodged within glomerular capillaries modulated VEGF/sFlt1 levels, thus preventing further endothelial damage, possibly by activating endogenous repair mechanisms. Specifically, it was confirmed that AFSC release EVs that express various surface markers, including VEGFR1 and VEGFR2, and can modulate VEGF/VEGFRs signaling in damaged GEC by decreasing the bio-availability of excess VEGF. In conclusion, the data confirm the ability of AFSC to ameliorate renal damage and establish that their secreted EVs could target a specific signaling pathway re-establishing GEC function, thus representing a potentially new glomerulus-specific targeted intervention.

Materials and Methods

AFSC Culture, GFP Infection and Flt1 Knockout Experiments.

Clonal lines of AFSC were derived and cultured as previously described (10).

For GFP transfection, AFSC were seeded at a density of $2.5\times10^4/cm^2$ and transduced with LentiBrite GFP packaged lentiviral particles (Millipore, #17-10387) at 35MOI. Transduction efficiency was assessed by inverted fluorescence microscope (Leica DMI6000 B). $AFSC^{GFP}$ were selected by FACS (BD, FACSAria III) and used for EV isolation. $AFSC^{Flt-/-}$ were generated by using a shRNA Lentiviral Particles Transduction system (Santa Cruz Biotechnology, #sc-35395-V) following manufacturers' instructions. Seeded AFSC ($10,000/cm^2$) were transduced at 5MOI, and stable clones were selected via puromycin selection (10 μg/ml) for about 2 weeks.

The clone with the highest KO efficiency was used for collecting EVs.

Animal Models (WT Mice, Alport Mice, Alport-TektdT), AFSC Injections and AFSC In Vivo Tracking, Serum Creatinine and Proteinuria Measurements.

WT mice (C57BL/6 mice) and Alport mice (B6.Cg-Col4α5tm 1Yseg/J) were purchased from the Jackson Laboratory; colonies are well established and maintained in a homozygous scheme (10). The Alport-$Tek^{tdT}$ mice were generated by breeding Alport mice with endothelial specific Cre-driver mouse (B6.Cg-Tg(Tekcre)lYwa/J; Jackson Laboratories) and a Cre-reporter mouse (B6.Cg-Gt(ROSA) $26Sor^{tm14(Cag\text{-}td\text{-}Tomato)Hze}$/J; Jackson Laboratories); these mice express tdtomato (tdT) in all endothelial cells including GEC. To study disease progression n=24 WT and n=24 Alport mice were used and sacrificed at 1, 2, 3, 4, 5 and 6 months of age (n=4, each time point) to isolate glomeruli. For TEM analysis n=3 of WT and n=3 of Alport mice were used. For in vivo experiments n=10 of WT, n=10 of Alport mice non-injected and n=10 Alport mice injected with AFSC were used.

Mice were injected with 1×106 AFSC through the left ventricle at 3 month of age, before onset of proteinuria as published (10). Mice were sacrificed at 2 (n=5) and 7 (n=5) weeks post injections. For cell tracking, 6 additional Alport mice were injected with AFSC pre-labeled with Qdot (or CM-Dil) immediately before the procedure (Invitrogen). The animals were killed at 5 days (n=3), and 10 weeks (n=3) after treatment, and four major organs (the heart, kidney, liver, and lung) were processed for FACS analysis as previously described (10).

A non-injected littermate served as the negative control throughout the analysis for each time point.

Blood samples and urine were collected as published (10). Serum creatinine was assessed by colorimetric assay (BioAssay Systems, #DICT-500) and albumin-to-creatinine ratio was determined using an ELISA for albuminuria (Immunology Consultants Laboratory, #E90AL) following manufacturers' instructions. All animal experiments were performed in adherence to the National Institutes of Health Guidelines for the Care and Use of Laboratory Animals and with local Institutional Animal Care and Use Committee approval.

Glomeruli and GEC Isolation

Glomerulus isolation was performed as previously described (10) and GEC from Alport-$Tek^{tdT}$ (n=8) were isolated by further digesting the glomeruli with 0.25% trypsin (Gibco, ThermoFisher Scientific)/0.6% collagenase IV (Worthington) solution in basal media supplemented with phosphatase inhibitors (ThermoFischer Scientific) for 20' at 37° C. Cells were then passed through a strainer and GEC were flow sorted using FACSAria III (Becton Dickinson).

EVs Isolation, Characterization and Labeling

EVs were isolated from supernatants of AFSC cultured overnight in RPMI-1640 (Lonza) without Fetal Calf Serum (25). Supernatants were centrifuged at 6,000 g for 20' and ultracentrifuged at 100,000 g (Optima L-100K ultracentrifuge; Beckman Coulter) for 2 hours at 4° C.; pellets were resuspended in serum-free RPMI-1640 containing 1% DMSO and stored at −80° C. until use.

EVs were characterized by cytofluorimetric analysis (28). EVs were analyzed using the following fluorescein isothiocyanate (FITC), phycoerythrin (PE) or allophycocyanin (APC) conjugated rat antibodies. Briefly, AFSC-EVs ($1\times10^9$ particles) were incubated for 15' at 4° C. and immediately acquired by FACS analysis using a Guava easyCyte™ Flow Cytometer (Millipore) and analyzed with InCyte software. Fluorochrome conjugated rat non-immune isotypic immunoglobulin G (Miltenyi Biotec) was used as control. The size and distribution of the AFSC-EVs was analyzed using a NanoSight LM10 instrument (NanoSight Ltd.) equipped with the nanoparticle tracking analysis (NTA) 2.0 analytic software.

RNA isolated using the mirVana RNA isolation kit (Ambion), was analyzed using miScript Reverse Transcription Kit and miScript SYBR Green PCR Kit (both from Qiagen). Fold change in miRNA expression was calculated as $2^{-\Delta Ct}$ using the snoRNA RNU6b as normalizer (28). A quantitative real-time polymerase chain reaction (qRT-PCR) was performed using a 96-well StepOne™ Real-Time System (Applied Biosystems) in order to analyze the EVs miRNA content. The sequence-specific oligonucleotide primers were all obtained from MWG-Biotech (mwg-biotech.com).

Western Blotting, Immunostaining, TEM, GEC Quantification, VEGF and sFlt1 ELISA, PCR, PCR Array.

Western blotting, immunostaining, PCR and PCR array were performed as previously published (10, 29). Details on procedures and list of antibodies and primers are described below. TEM analysis was performed as published (10) and expression for VEGF and sFlt1 in glomerular extracts, serum and in cell culture supernatants were assessed by Enzyme linked immunosorbent assays according to manufacturers' instructions (RayBiotech, #ELM-VEGF and #ELM-VEGFR1). GEC fenestration size was evaluated in 20 randomly selected TEM images per sample (n=3) with a field of view at 28,000×. The surface areas of the fenestrations adjacent to the GBM were quantified by ImageJ software (NIH). Briefly, with a 8-connect Wand Tool the fenestrations were individually selected and pixel width and height were used to calculate the area. All measurements were done in a double-blinded fashion.

Co-Immunoprecipitation Assay.

To evaluate VEGF/VEGFR1 interactions between VEGFR1 expressed by EVs and the excess of VEGF described in the in-vitro experiments, immunoprecipitation for VEGFR1 using VEGFR1 antibody and Protein G-agarose conjugate (Santa Cruz) was applied overnight at 4° C. Immunoprecipitates were collected by centrifugation at 1,000×g for 5' at 4° C., washed with PBS and resuspended in electrophoresis sample buffer, denatured and ran under reducing conditions as previously described (10). The immunoblots were then probed for VEGF detection using VeriBlot-HRP conjugated secondary antibody (Abcam) and standard Western Blotting techniques as previously described (10).

In Vitro Co-Culture of GEC-AFSC and GEC-EVs

GEC were seeded at $1\times10^4$ cells/$cm^2$ and cultured at 37° C. and 5% $CO_2$ in basal medium supplemented with 0.1% VEGF, 0.1% ECGS, 0.1% Heparin, 0.1% EGF, 0.1% Hydrocortisone, 1% L-Glutamine, 1% antibioticantimycotic solution, 5% FBS (CellBiologics). GEC were overstimulated with recombinant mouse VEGF (Gibco, ThermoFisher Scientific) applied at 100 ng/ml. Simultaneously, AFSC (ration 1:1, on transwell inserts, Corning) or EVs and $EV^{Flt-/-}$/(10,000:1 ratio, on culture media) were co-cultured with GEC under the same growth conditions. Experiments were terminated at 24 and 48 hours and culture media and cells were collected for analysis. Integration of EVs into GEC was performed by applying EVs with green and red fluorescence tags derived from AFSCGFP co-labeled with CM-Dil as previously reported (10) (ThermoFischer Scientific) to GEC overnight. Integration of EV into GEC was assessed by inverted fluorescence microscope (Leica DMI6000 B). Experiments were repeated in triplicate.

Statistical Analysis

Data are expressed as means±SEM or as means±SD. Two-tailed Student's t-test was used for comparisons between two groups. Mann-Whitney test was used to compare data sets with non-normal distribution. One-way analysis of variance was used for comparison of three or more groups. All statistical analyses were done with GraphPad Prism software version 7.0 (GraphPad Software, Inc.). p-values of <0.05 were considered significant.

Western Blot

Total protein from glomeruli and cultured GEC were collected and stored at −80° C. in a radioimmunoprecipitation assay buffer supplemented with protease and phosphatase inhibitors (ThermoFischer Scientific) until use. Protein electrophoresis was performed on 4-20% Tris-Glycine gels and transferred onto a polyvinylidene fluoride 0.45-μm membrane (Millipore) and probed with antibodies with overnight incubation at 4° C. HRP-conjugated secondary anti-rabbit antibodies (Sigma-Aldrich) were applied it 1:20,000 ratio. Antigens were detected using the ECL Western Blotting detection reagents (Amersham Biosciences/GE Healthcare), impressed on Biomax Light Film (GE Healthcare). Data from 3 independent experiments were quantified by densitometry (all measurements were normalized against their corresponding housekeeping gene, β-actin).

Immunohistochemistry

Thin deparaffinized kidney sections (5 μm) were blocked in 3% BSA and immunostained for fluorescence microscopy with antibodies applied overnight at 4° C. (see Table below). Alexa Fluor conjugated secondary antibodies (ThermoFisher Scientific) were applied at 1:500 dilution with 30' incubation at room temperature. A Leica DM RA fluorescent microscope was used in conjunction with Open Lab 3.1.5 software to image the staining.

Real-Time PCR and PCR Array

Total RNA from GEC sorted out of the $Tek^{tdT}$ Alport and WT kidneys was extracted using Qiagen RNeasy kit according to the manufacturers' instructions. To characterize these GEC quantitative real-time PCR for AKT, CD31, PDGFRβ, VEGFR2 and WT1 was carried out using a Roche Light Cycler 480 and Light Cycler TaqMan Master Mix as previously described (10). To evaluate GEC damage in vitro as well as the ability of AFSC to modulate VEGF gene expression in GEC was analyzed using the mouse endothelial cell biology RT2 Profiler PCR Array System according to the manufacturers protocols (Qiagen) and as previously described (10). Briefly, 250 ng of total GEC RNA were used in the synthesis of template DNA using the RT2 First Strand Kit according to the manufacturer's protocols (Qiagen). RT-PCR data were analyzed using the online real-time PCR analysis module by Qiagen.

TABLE 1

List of Antibodies for Western Blotting and immunostaining (cells)

| Antibody | Company | Catalogue Number | Dilution |
|---|---|---|---|
| VEGF | Abcam | ab46154 | WB: 1:100 IF: 1:200 |
| VEGFR1 | Abcam | ab2350 | WB: 1:200 |
| pVEGFR2(Tyr951) | Cell signaling | 4991 | WB: 1:500 |
| Beta-actin | Gentex | 109639 | WB: 1:1000 |
| VE-Cadherin | Abcam | ab33168 | IF: 1:100 |
| CD31 | Pharmingen | 553370 | IF: 1:200 |
| CD2AP | Santa Cruz | 34229 | IF: 1:50 |

TABLE 2

List of Antibodies for Flow Cytometry (EVs)

| Antibody | Company | Catalogue Number | Dilution |
|---|---|---|---|
| CD29 | Miltenyl Biotec | 130-102-975 | 1:300 |
| CD44 | Miltenyl Biotec | 130-102-977 | 1:300 |
| CD73 | Miltenyl Biotec | 130-103-054 | 1:300 |
| CD90 | Miltenyl Biotec | 130-102-636 | 1:300 |
| CD105 | Miltenyl Biotec | 130-102-915 | 1:300 |
| CD146 | Miltenyl Biotec | 130-102-846 | 1:300 |
| CD9 | Miltenyl Biotec | 130-102-579 | 1:300 |
| CD24 | Miltenyl Biotec | 130-103-370 | 1:300 |
| TIE2 | eBioscience | 12-5987-81 | 1:300 |
| CD63 | R&D Systems | MAB5417 | 1:300 |
| VEGFR1 | R&D Systems | AF471 | 1:300 |
| VEGFR2 | R&D Systems | AF644 | 1:300 |
| NEUROPILIN-I | R&D Systems | AF566 | 1:300 |
| NEUROPILIN-II | R&D Systems | AF567 | 1:300 |

TABLE 3

List of Primers for qPCT (cells/tissue)

| Primer | Sequence | Probe |
|---|---|---|
| AKT | 5'-tcgtgtggcaggatgtgtat-3' (SEQ ID NO: 1) 5'-acctggtgtcagtctcagagg-3' (SEQ ID NO: 2) | 45 |
| CD31 | 5'-actcgacaggatggaaatcac-3' (SEQ ID NO: 3) 5'-cggtgttcagcgagatcc-3' (SEQ ID NO: 4) | 45 |

TABLE 3-continued

| List of Primers for qPCT (cells/tissue) | | |
|---|---|---|
| Primer | Sequence | Probe |
| PDGFRb | 5'-tcaagctgcaggtcaatgtc-3' (SEQ ID NO: 5) 5'-ccattggcagggtgactc-3' (SEQ ID NO: 6) | 32 |
| VEGF | 5'-caggctgctgtaacgatgaa-3' (SEQ ID NO: 7) 5'-gctttggtgaggtttgatcc-3' (SEQ ID NO: 8) | 9 |
| VEGFR1 | 5'-atccctcggccaacaatc-3' (SEQ ID NO: 9) 5'-cattctcagtgcagaagtcatacc-3' (SEQ ID NO: 10) | 21 |
| VEGFR2 | 5'-cagtggtactggcagctagaag-3' (SEQ ID NO: 11) 5'-acaagcatacgggcttgttt-3' (SEQ ID NO: 12) | 68 |
| WT1 | 5'-cagatgaacctaggagctaccttaaa-3' (SEQ ID NO: 13) 5'-tctgcccttctgtccatttc-3' (SEQ ID NO: 14) | 3 |
| 18S | 5'-aaatcagttatggttcctttggtc-3' (SEQ ID NO: 15) 5'-gctctagaattaccacagttatccaa-3' (SEQ ID NO: 16) | 55 |

TABLE 4

| List of primers for miRNAs (EVS) | |
|---|---|
| miR-10b-5p | 5-uacccuguagaaccgaauuugug-27 (SEQ ID NO: 17) |
| miR-126a-3p | 46-ucguaccgugaguaauaaugcg-67 (SEQ ID NO: 18) |
| miR-132-3p | 42-uaacagucuacagccauggucg-63 (SEQ ID NO: 19) |
| miR-210-3p | 66-cugugcgugugacagcggcuga-87 (SEQ ID NO: 20) |
| miR-15a-5p | 15-uagcagcacauaaugguuugug-36 (SEQ ID NO: 21) |
| miR-16-1-5p | 16-uagcagcacguaaauauuggcg-37 (SEQ ID NO: 22) |
| miR-93-5p | 15-caaagugcuguucgugcagguag-37 (SEQ ID NO: 23) |
| miR-200b-3p | 45-uaauacugccugguaaugauga-66 (SEQ ID NO: 24) |
| miR-322-5p | 23-cagcagcaauucauguuuugga-44 (SEQ ID NO: 25) |
| miR-21a-5p | 18-uagcuuaucagacugauguuga-39 (SEQ ID NO: 26) |
| miR-23a-3p | 46-aucacauugccagggauuucc-66 (SEQ ID NO: 27) |
| miR-27a-3p | 56-uucacaguggcuaaguuccgc-76 (SEQ ID NO: 28) |
| miR-145a-5p | 7-guccaguuuucccaggaaucccu-29 (SEQ ID NO: 29) |

TABLE 4-continued

| List of primers for miRNAs (EVS) | |
|---|---|
| miR-218-1-5p | 25-uugugcuugaucuaaccaugu-45 (SEQ ID NO: 30) |
| miR-221-3p | 60-agcuacauugucugcuggguuuc-82 (SEQ ID NO: 31) |

Results

VEGF/VEGFRs/sFlt1 Signaling Characterization within Alport Glomerulus

To investigate the role of VEGF in AS progression, it was determined if VEGF signaling is altered within the glomeruli of Alport mice. The VEGF isoform we studied is the VEGF-A.

Figure 1B:
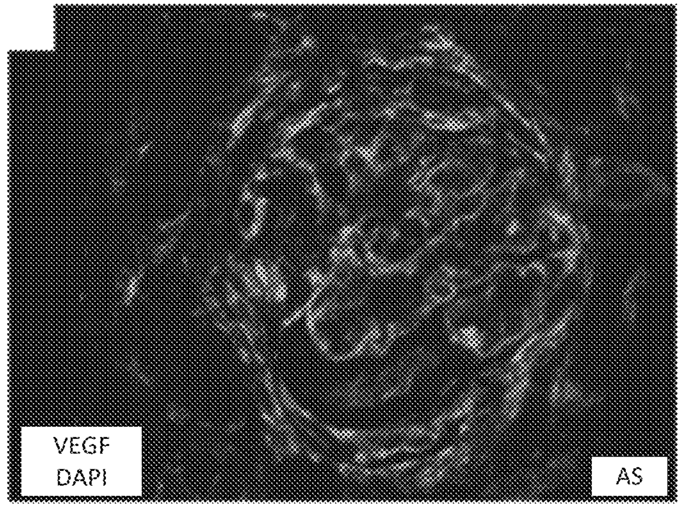
Figure 1C:
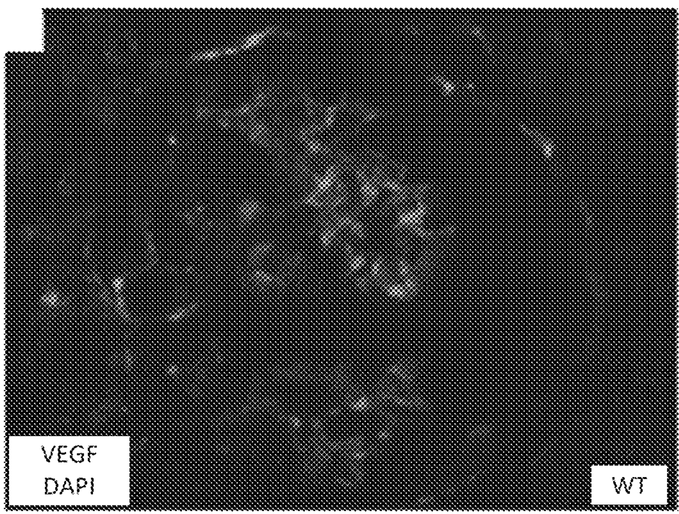
Figure 1E:
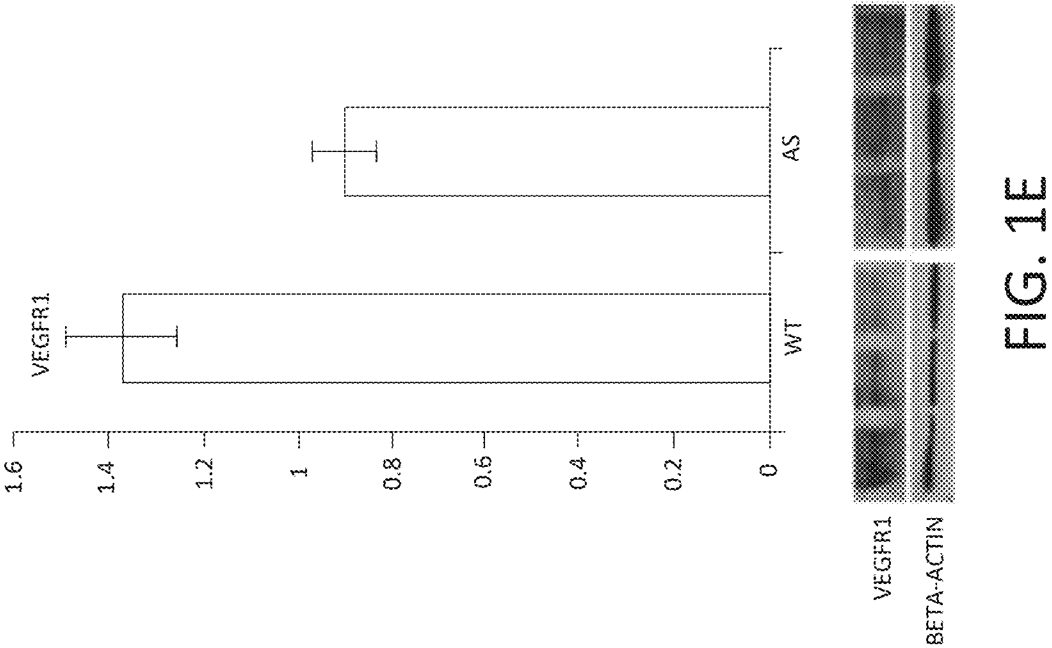
Figure 1D:
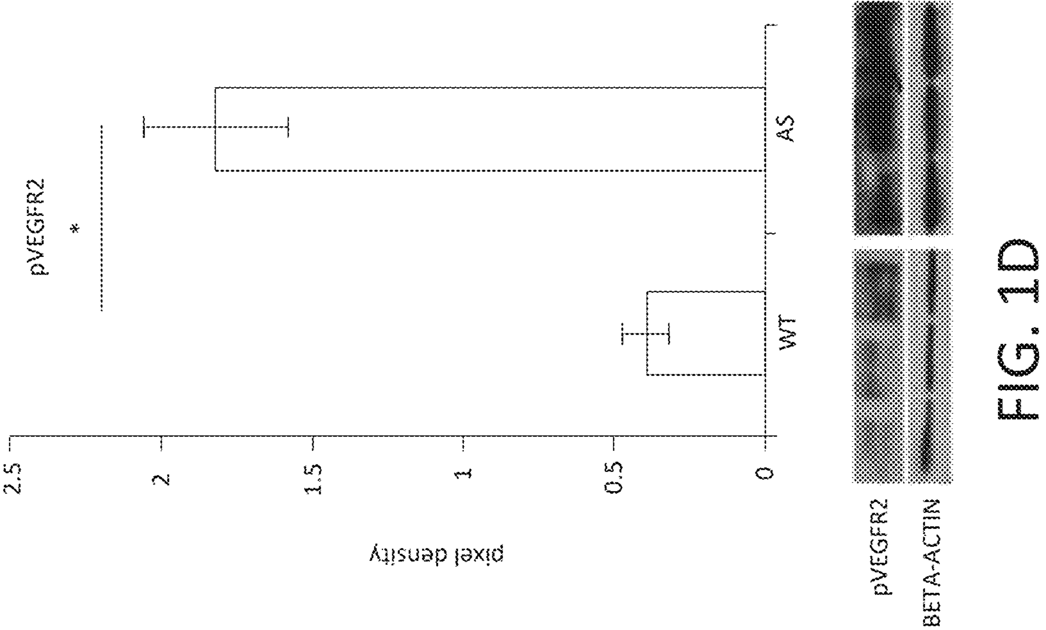
Figure 1F:
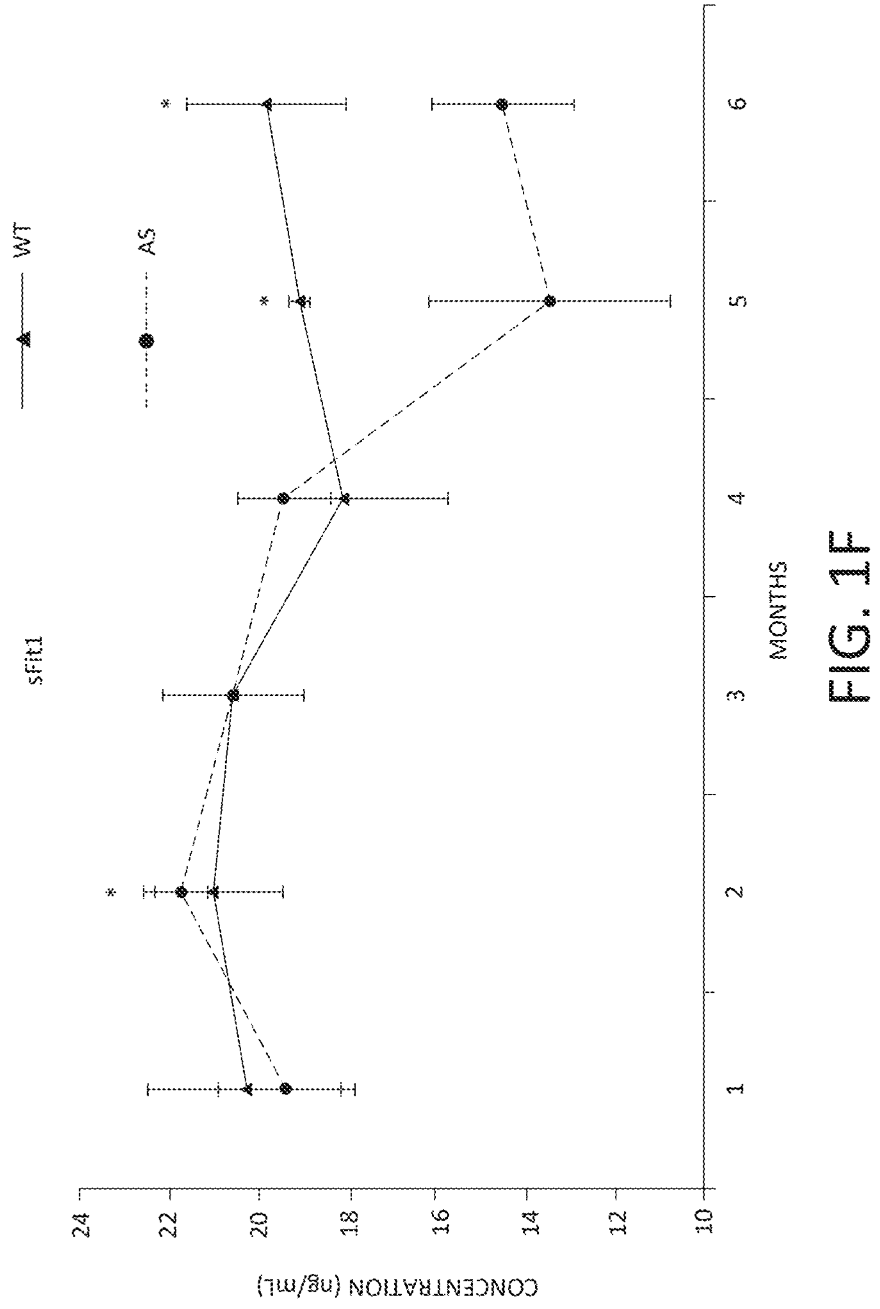
Figure 1G:
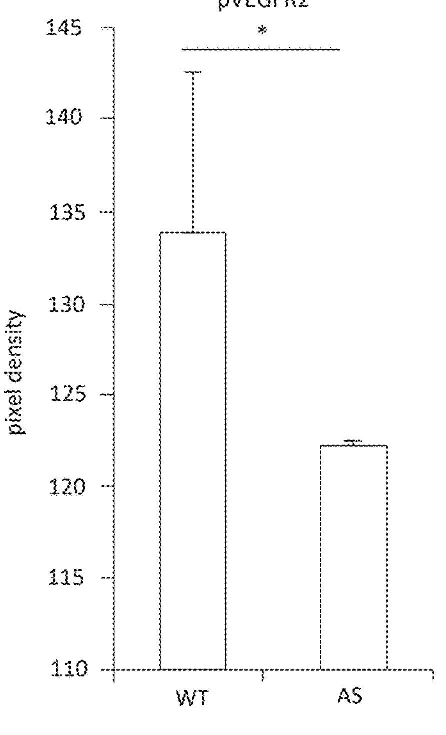
Figure 1H:
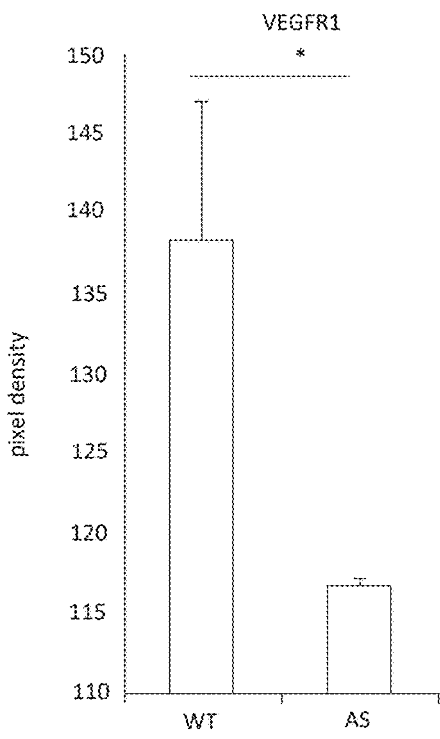

As shown in FIG. 1A-C, VEGF expression was markedly altered early on in disease that peaked at 3 months, but decreased later on. VEGF over-activation was shown by increased pVEGFR2 (FIG. 1D). Although VEGFR1 expression at 3 months of age didn't shift significantly (FIG. 1E), its soluble form (sFlt1) was significantly decreased in later disease stages (5-6 months of age) (FIG. 1F). At 6 months of age, both pVEGFR2 and VEGFR1 expression were downregulated (FIG. 1G-H), likely indicating that glomerular cells counter-react the VEGF signaling alteration at this time by turning down the sensitivity to the signal.

GEC Characterization in Alport Mice

Figure 2A:
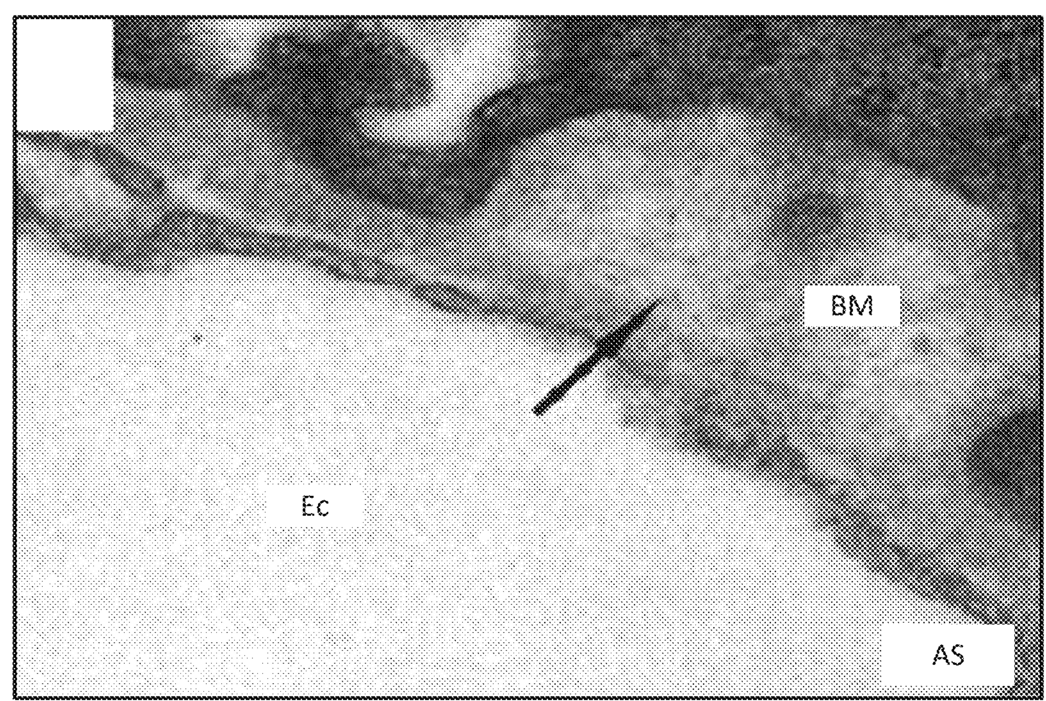
Figure 2B:
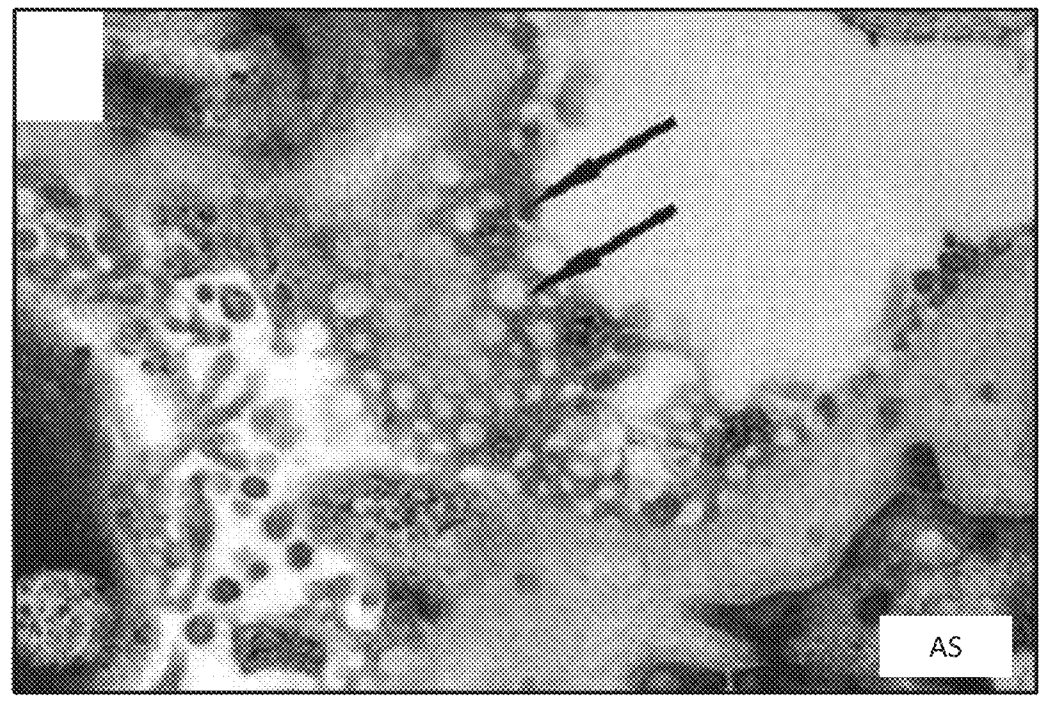
Figure 2C:
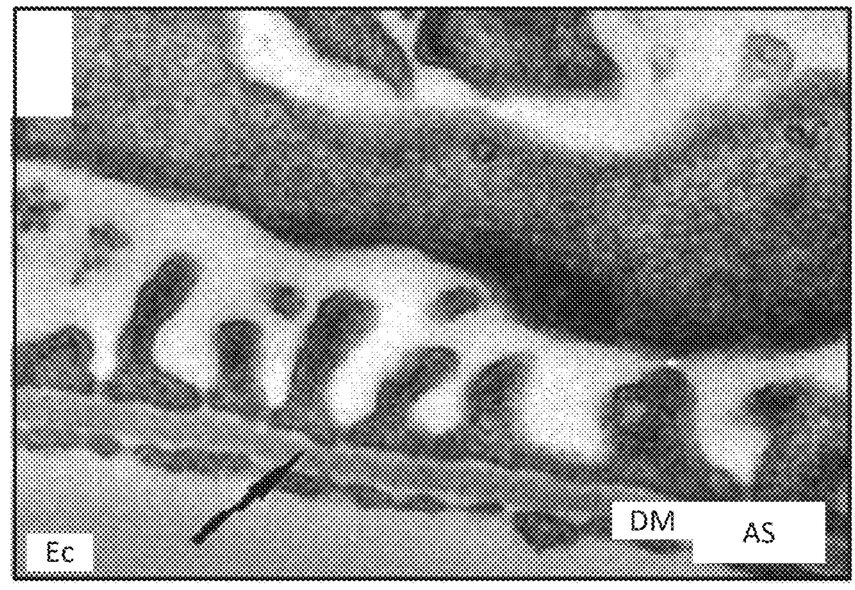
Figure 2D:
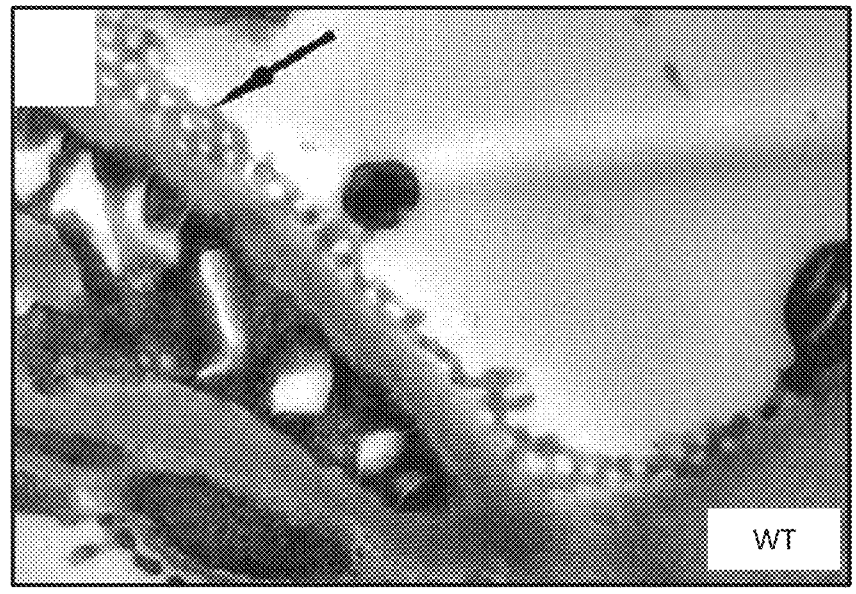

It was next examined the impact of VEGF modulation on GEC. As shown by TEM, GEC presented an altered morphology characterized by disruption of fenestrations when compared to WT (FIG. 2A-D) at 3 months of age. TEM scans showed characteristic splitting of the GBM consistent with AS pathology, whereas WT mice had normal basement membrane thickness (FIG. 2C-D, black arrows). Fenestration size was significantly increased in Alport mice further confirming changes in GEC morphology (FIG. 2A, E) during VEGF peak expression.

Figures 2H, 2I, 2J:
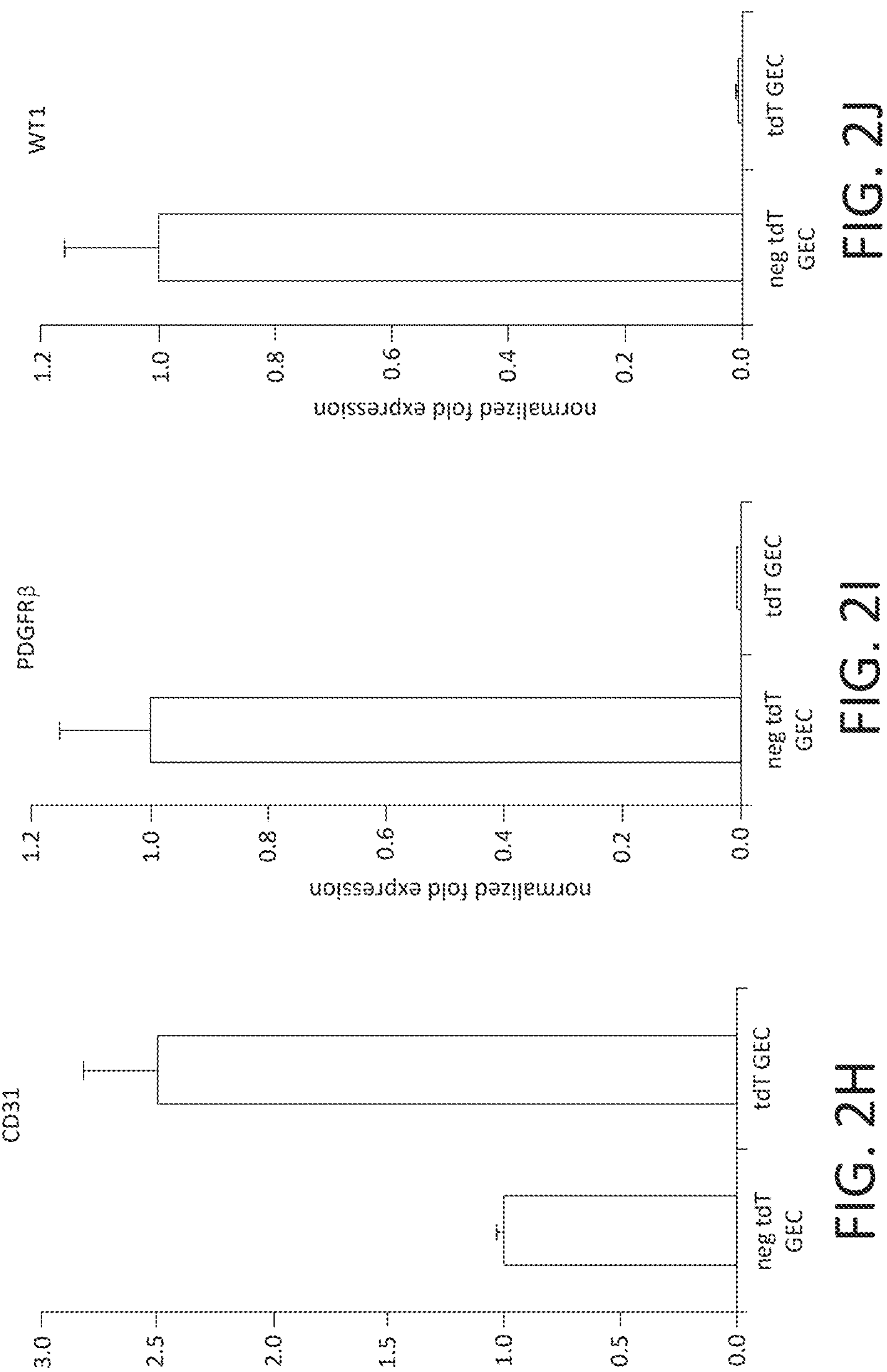
Figure 7A:
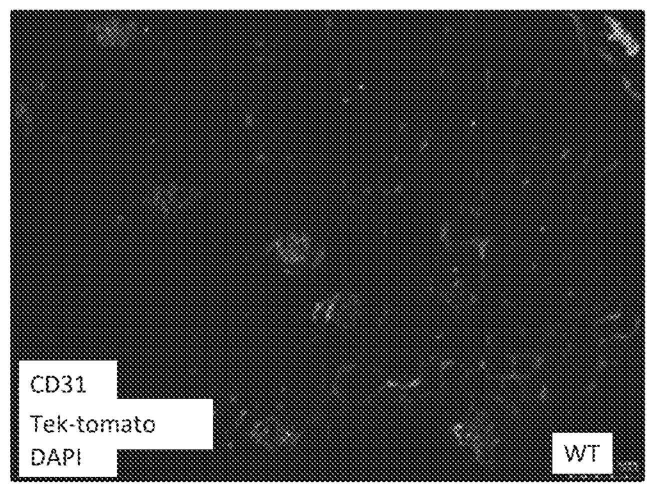
Figure 7B:
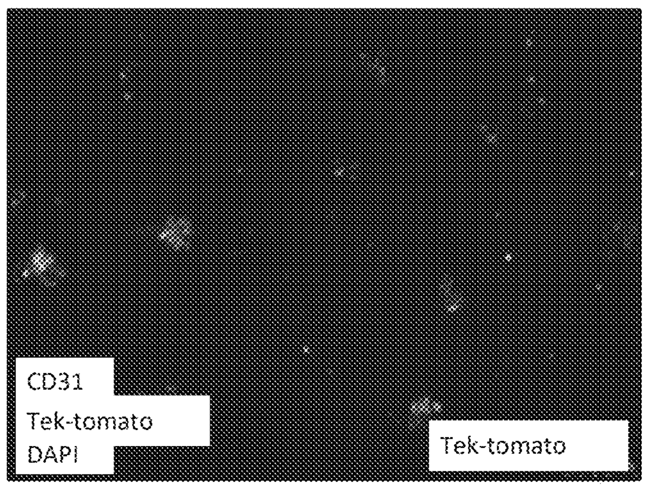
Figure 7C:
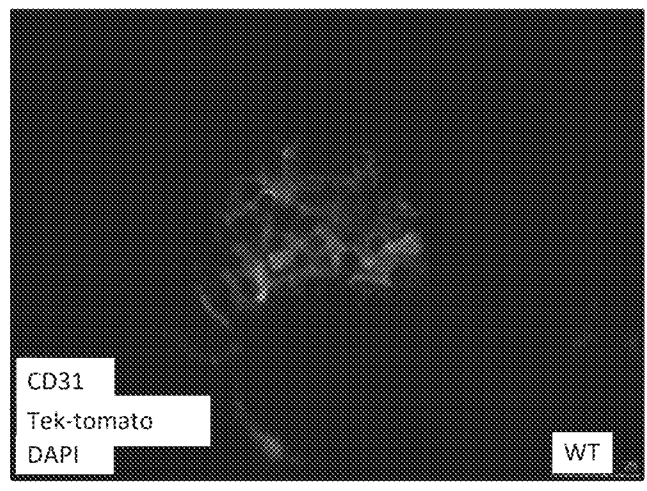
Figure 7D:
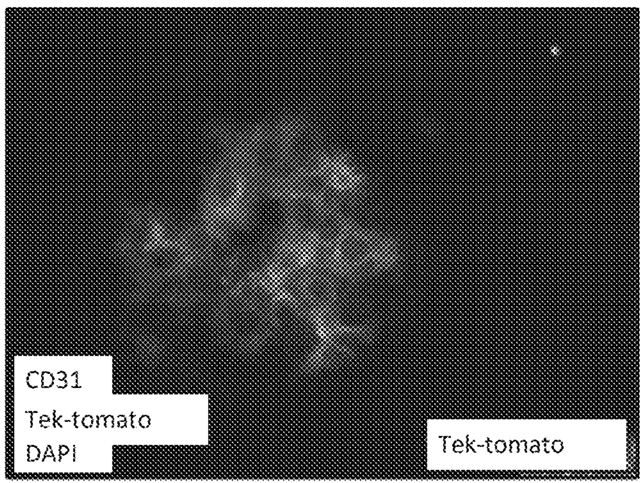
Figure 7E:
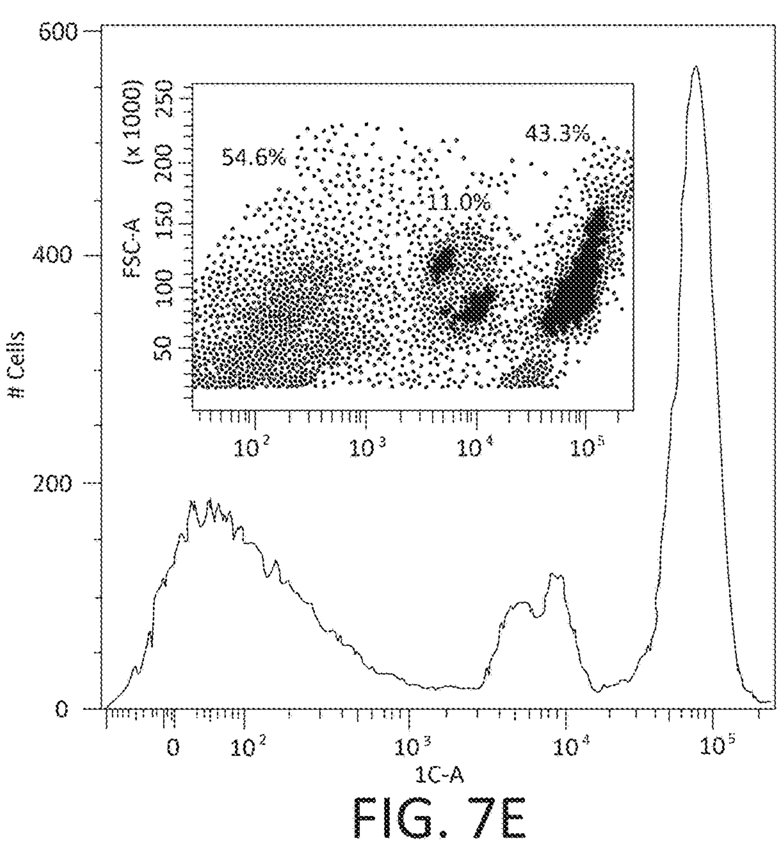
Figure 7F:
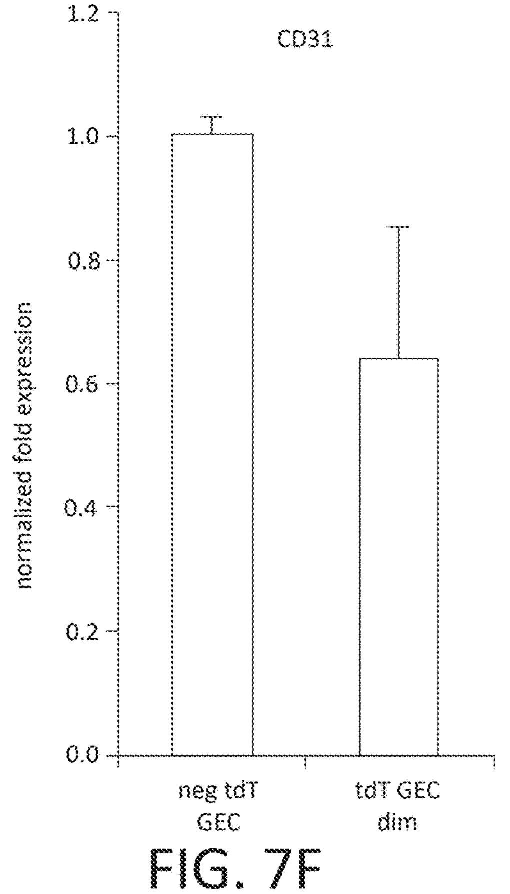
Figure 7G:
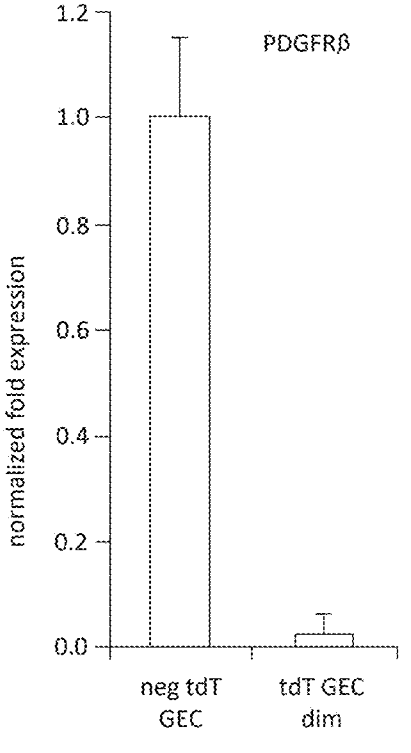
Figure 7H:
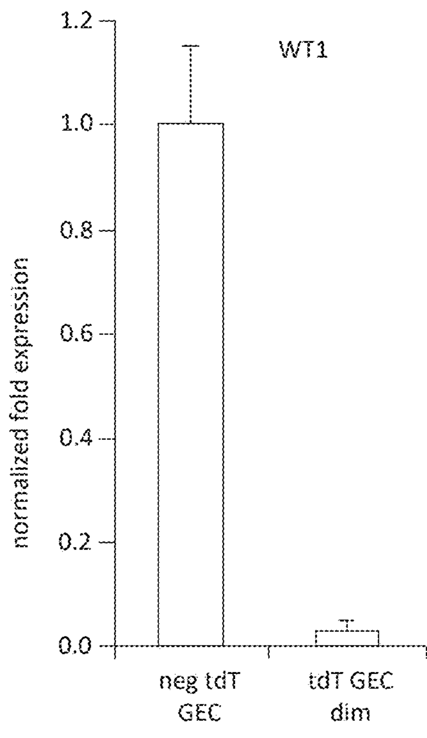

To study GEC biology and the correlation between GEC damage and VEGF modulation, Alport mouse with fluorescently labeled GEC (Alport-Tek$^{tdT}$) was generated, among other endothelial cells in other organs. It was confirmed that glomeruli from WT-Tek$^{tdT}$ mice present with strong tdTomato (tdT) signal (in red) in GEC (FIG. 7A-E, FIG. 8F-G]. Of note, two distinct populations of tdT positive were identified within the glomerulus, represented with bright and dim tdT expression (FIG. 7E). The FACS sorted bright tdT-GEC cells (FIG. 7E, FIG. 8G) were further confirmed for their endothelial phenotype for expression of CD31 by PCR (FIG. 2H. The tdT-GEC were negative for markers like PDGFRβ and WT1 (FIG. 2I-J); thus indicating that within the glomerulus, the tdT is expressed exclusively in GEC, allowing one to isolate GEC free from contamination of other glomerular cells. The dim population lacked strong expression of endothelial markers (FIG. 7E-H). Therefore the former was used in all the experiments described.

Figures 2K, 2L, 2M:
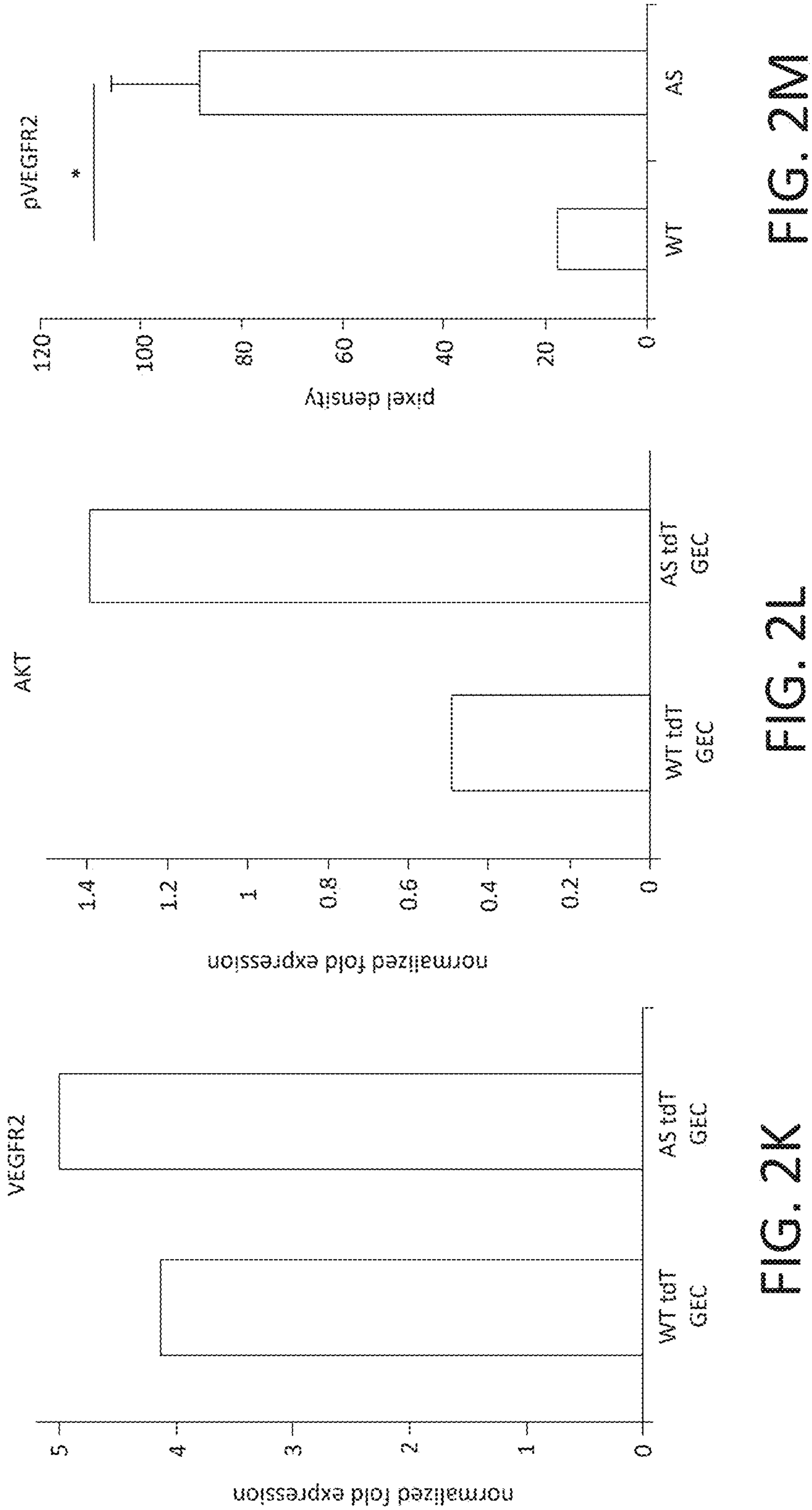

Isolated GEC from Alport-TektdT presented altered level of mRNA for VEGF and AKT (downstream VEGF signaling, (FIG. 2K-L)) and showed increased expression of pVEGFR2 (FIG. 2M).

AFSC Effects on Intraglomerular Regulation of VEGF Signaling and on GEC Biology

Figure 3A:
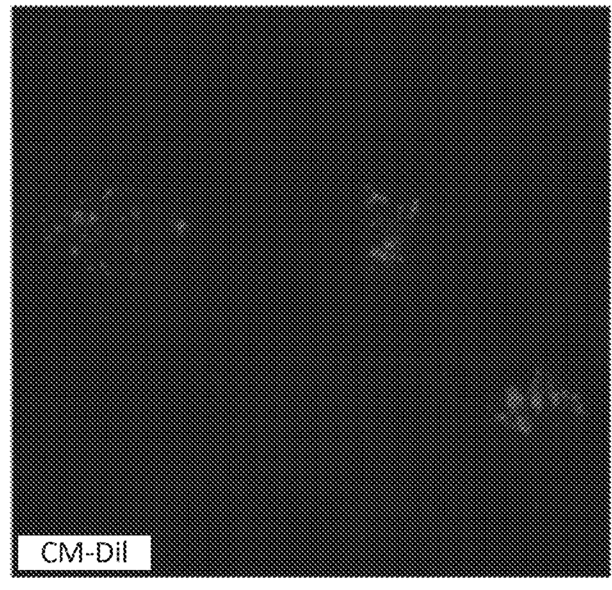
FIGS. 3A-I. AFSC homing to the kidney and modulation of VEGF, p-VEGFR2, VEGFR1 and sFlt1. Alport mice were injected at 3 months of age to study homing of AFSC and modulation of VEGF signaling. Injected labeled-AFSC (CM-Dil, red) were traceable after 5 days and could be detected by fluorescence within Alport glomeruli (A, 20×). Isolated glomeruli of Alport mice after 5 days of injection showed CM-Dil labeled AFSC in red (B, 10×; C, higher magnification 40×). Injection of AFSC modulated expression of p VEGFR2 (D, 230 KDa) and VEGFR1 (E, 151 KDa) within the glomeruli of Alport mice compared to non-injected siblings after 2 weeks of injection, restoring the activity of these VEGFRs almost at normal levels. Western Blot data were quantified by densitometry (all measurements were normalized against their corresponding housekeeping gene, β-actin, 42 KDa). As shown in graph F-G, injection of AFSC normalized levels of VEGF and sFlt1 measured by Elisa in Alport versus non-treated mice. WT mice were used as control; mice were sacrificed at 7 weeks after injection. Injection of AFSC also ameliorated serum creatinine (H) and proteinuria (1) in Alport mice Values are presented as mean±SEM (*p<0.05).
Figure 3B:
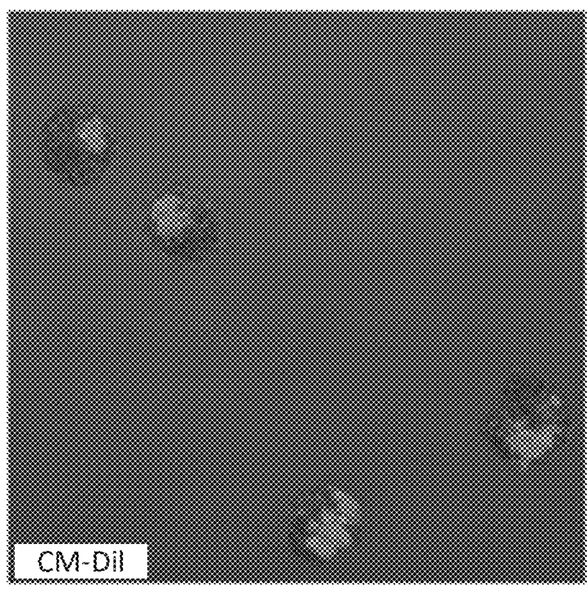
Figure 3C:
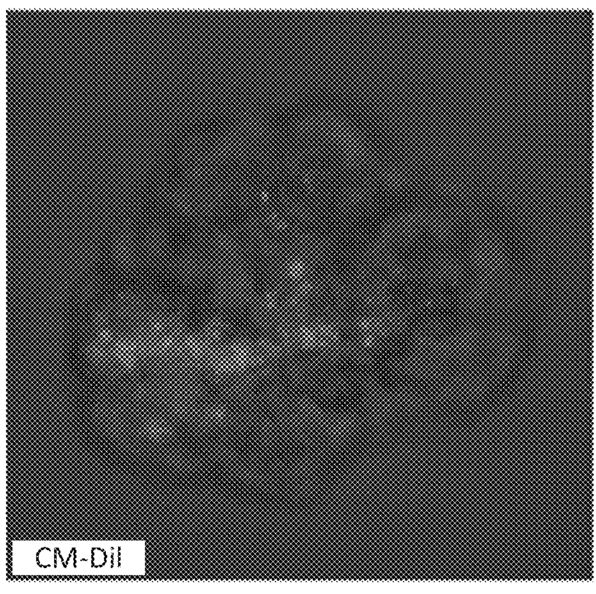
Figures 3D, 3E:
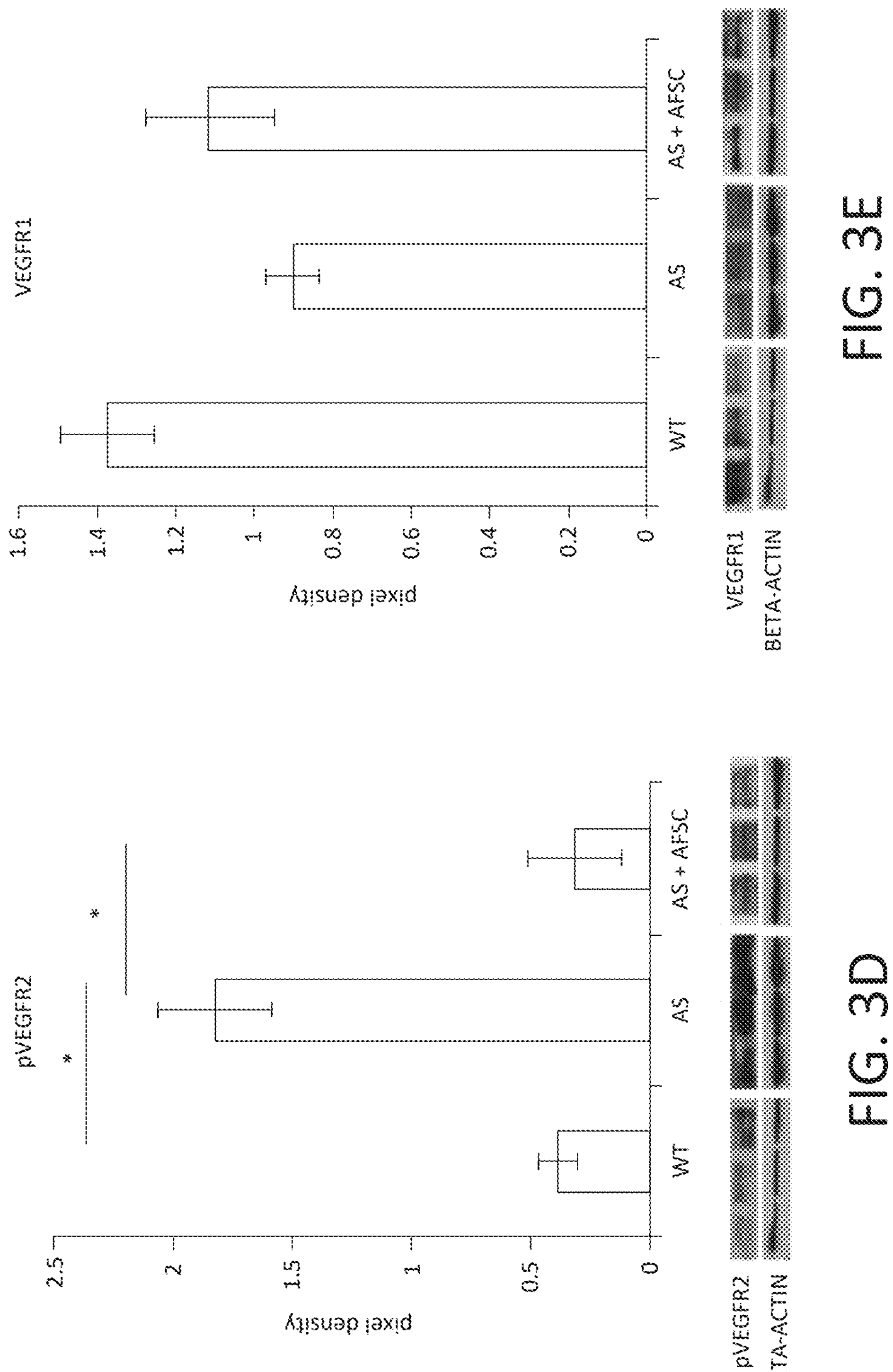
Figure 3G:
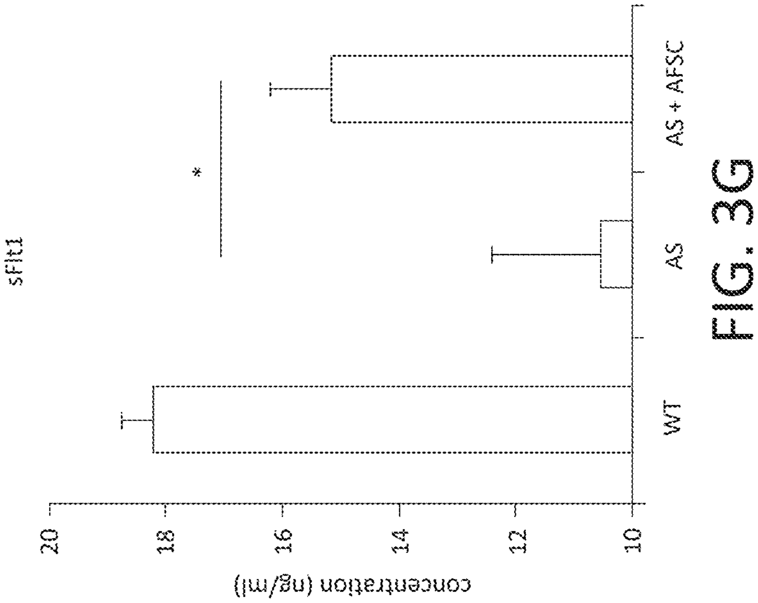
Figure 3F:
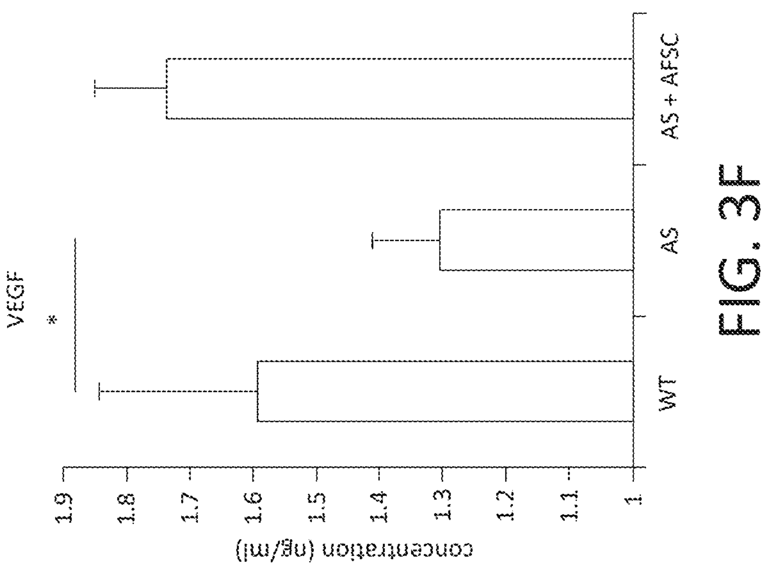
Figure 3H:
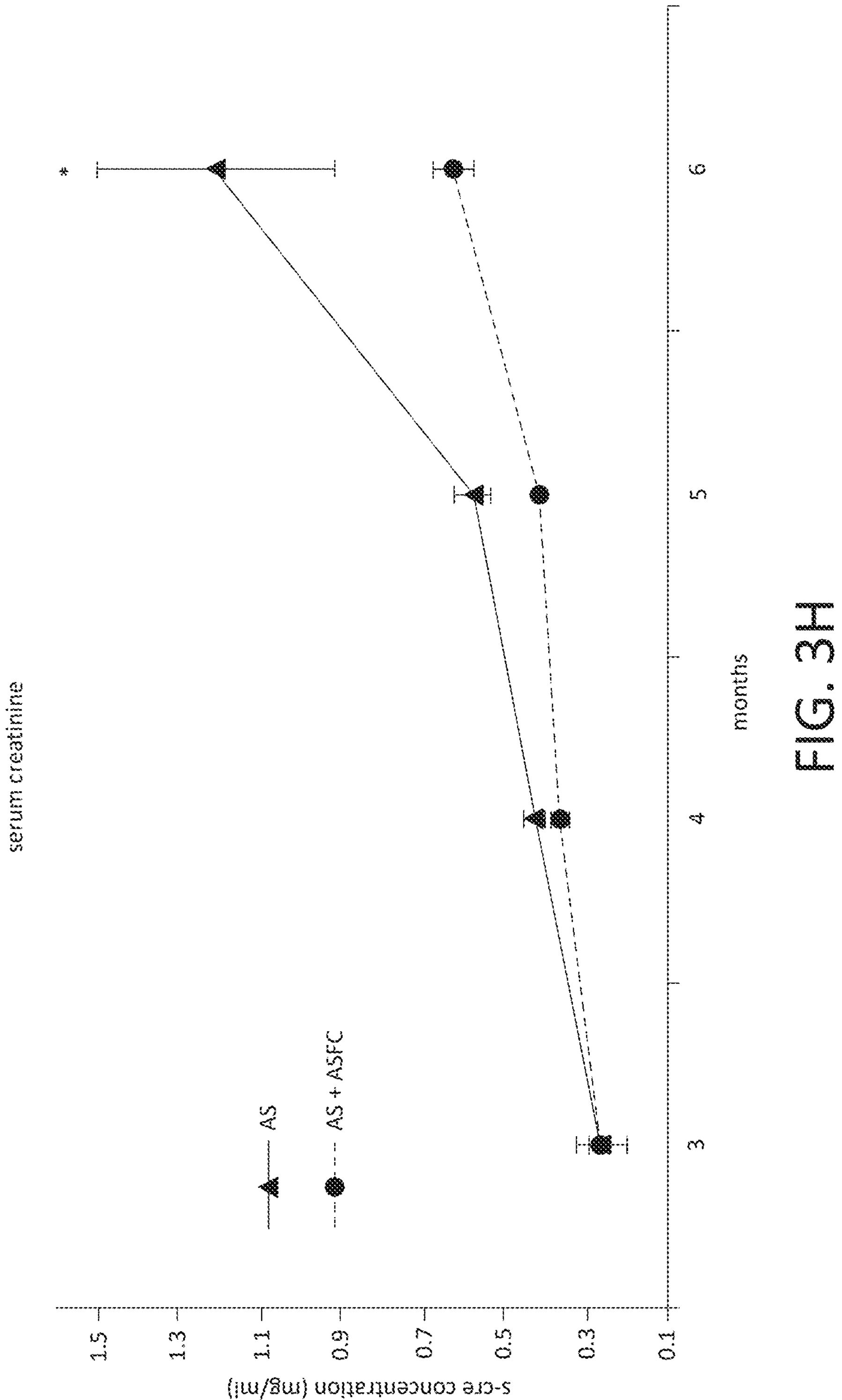
Figure 3I:
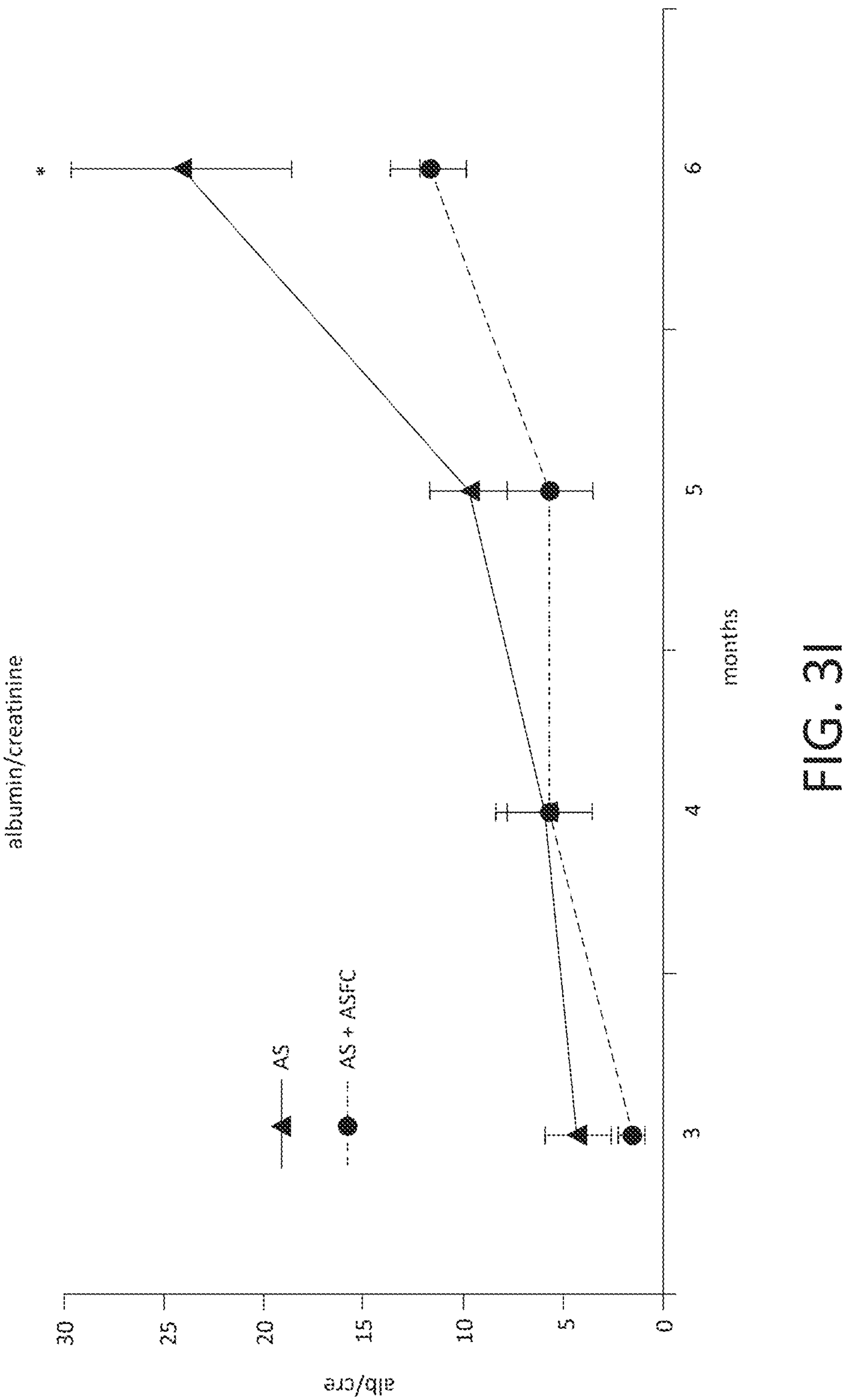
Figure 8A:
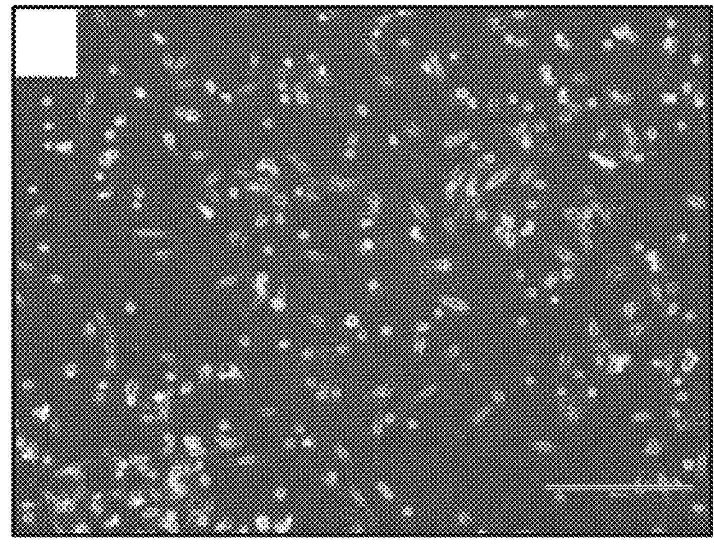
Figure 8B:
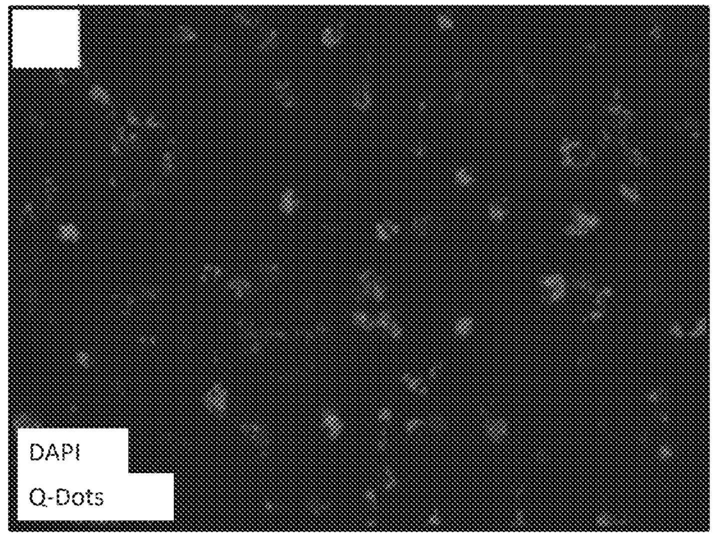
Figure 8C:
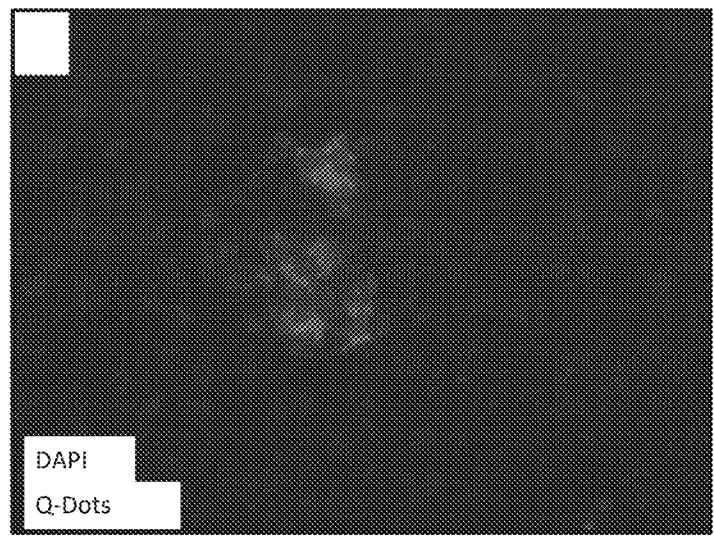
Figure 8D:
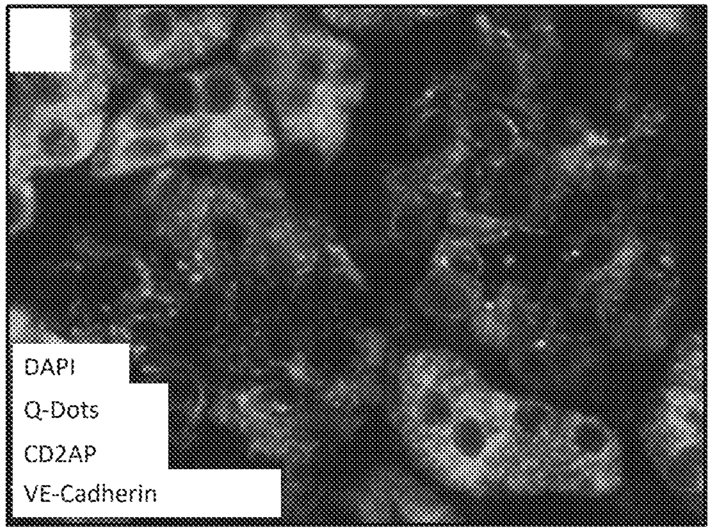
Figure 8E:
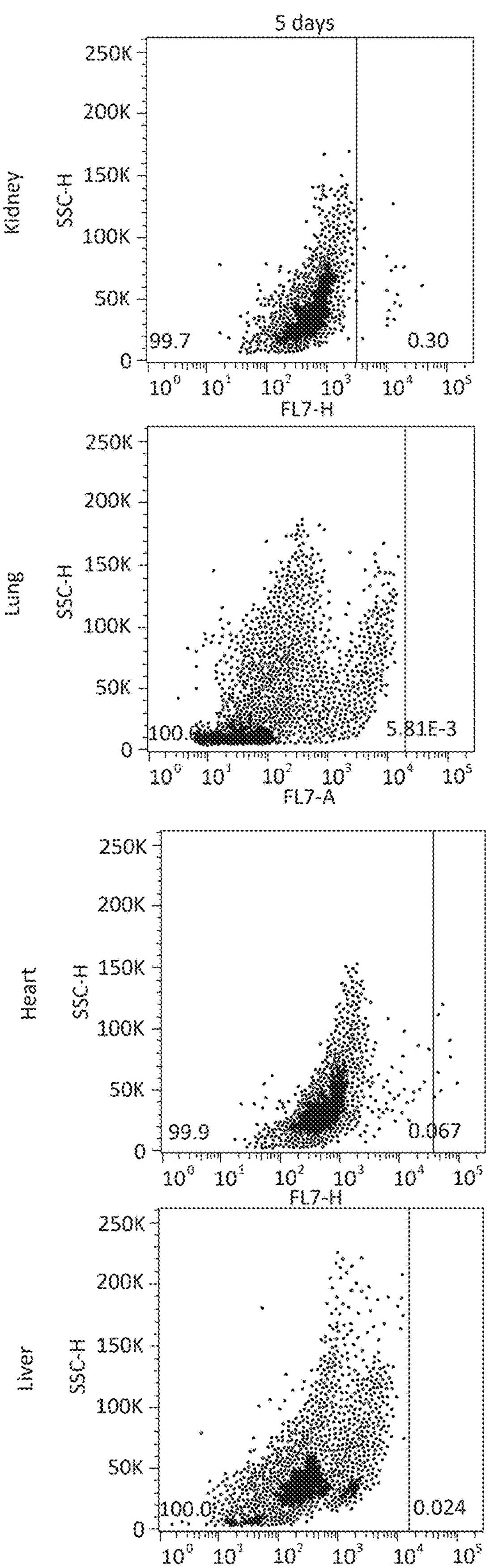
Figure 8F:
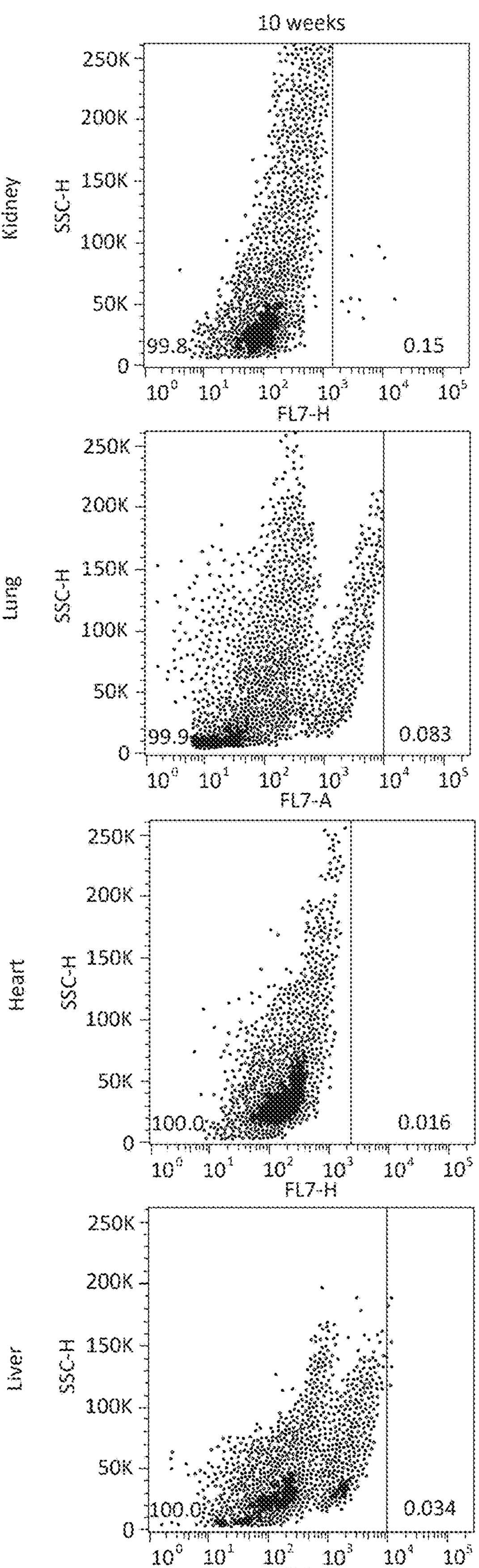

To study the modulation of VEGF signaling by AFSC, mice were treated with a single injection of CM-Dil or QDots tagged AFSC (the same cell line as published (10)) prior to onset of proteinuria (FIG. 8A-B]. AFSC localized predominantly within the kidney, specifically in glomeruli (FIG. 3A-C and FIG. 8C-D] in close association with GEC as shown by a co-staining with VE-cadherin (endothelial cells) and CD2AP (podocytes) (FIG. 8D) after 5 days of delivery. Cells were not found in other organs in any significant number (FIG. 8E-F], as previously reported (10). After 2 weeks of AFSC injection the expression of pVEGFR2 and VEGFR1 within the isolated glomeruli was comparable with that of the WT (FIG. 3D-E). After 7 weeks of injection VEGF and sFlt1 expression was comparable with that of the WT (FIG. 3F-G), followed by mitigation of serum creatinine and proteinuria in treated mice (FIG. 3H-I).

Figure 9A:
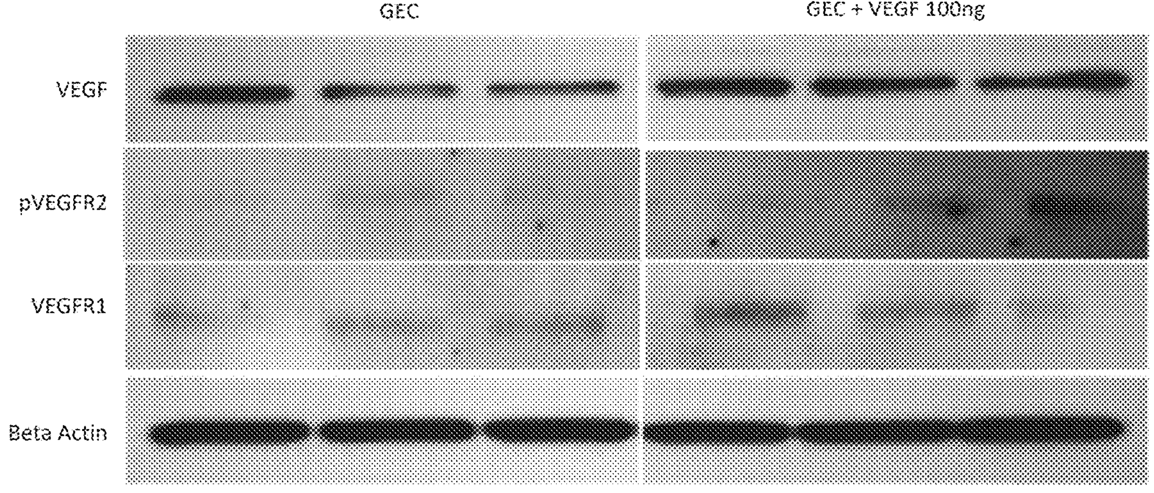
Figure 9B:
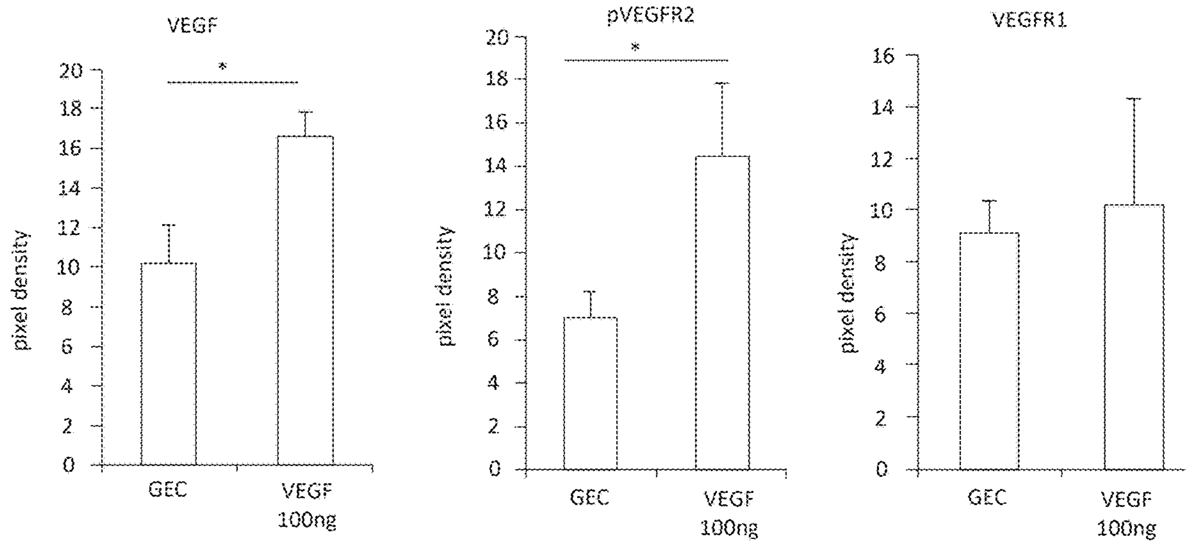
Figure 9C:
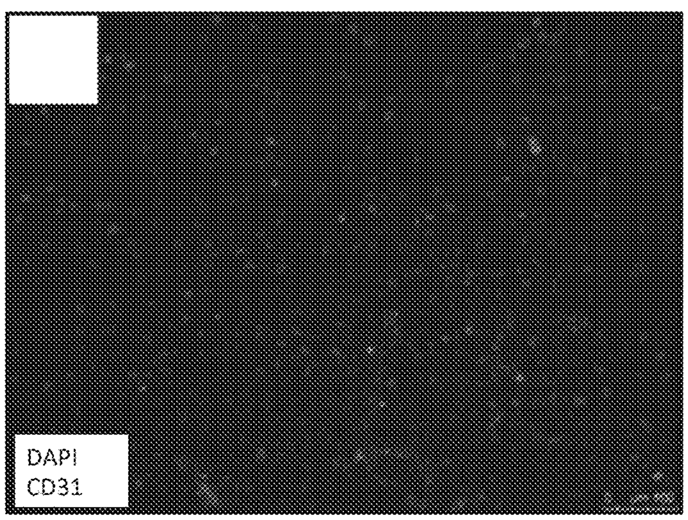
Figure 9D:
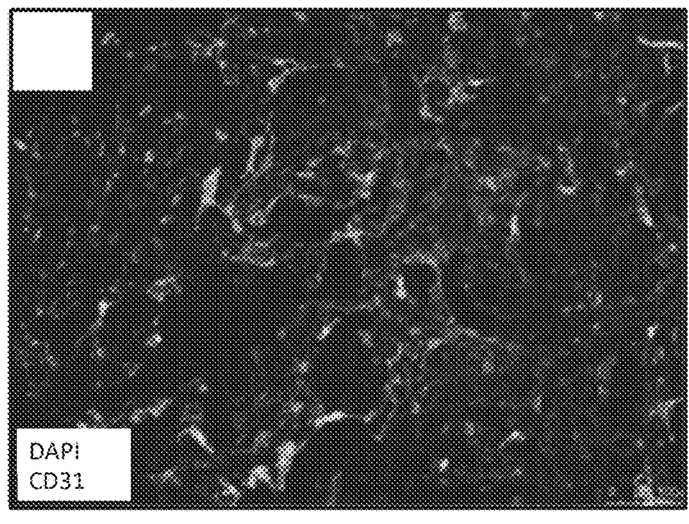
Figure 9E:
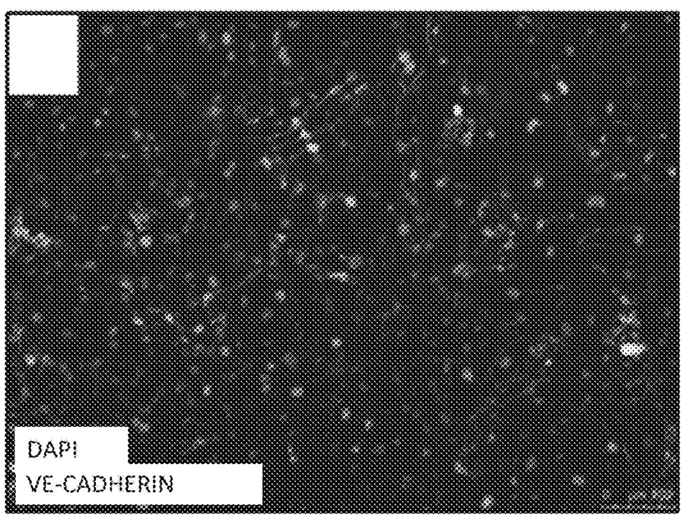
Figure 9F:
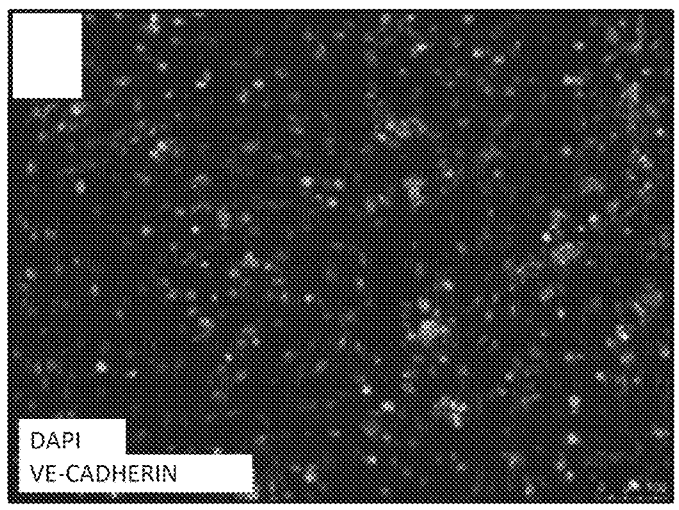
Figure 9G:
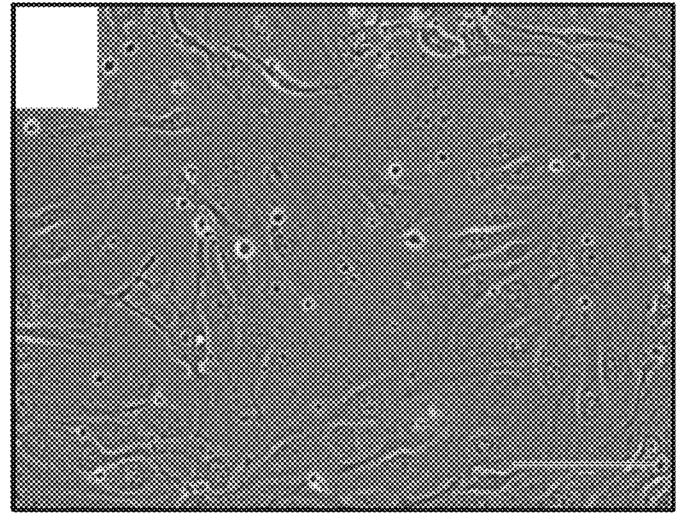
Figure 9H:
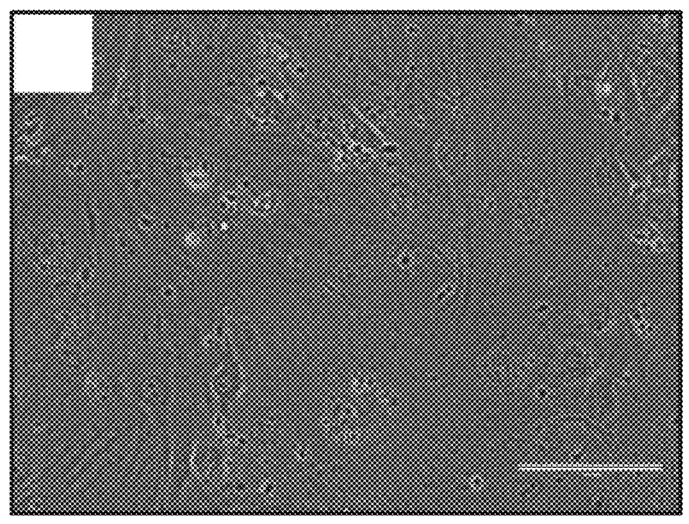
Figure 9I:
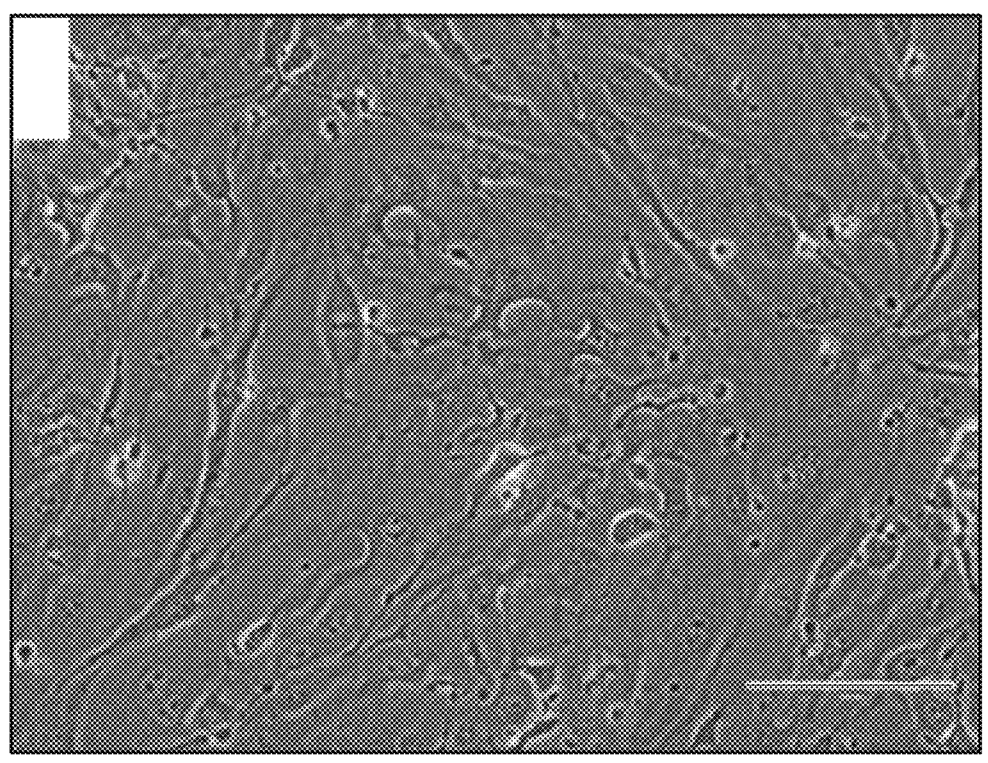
Figure 9J:
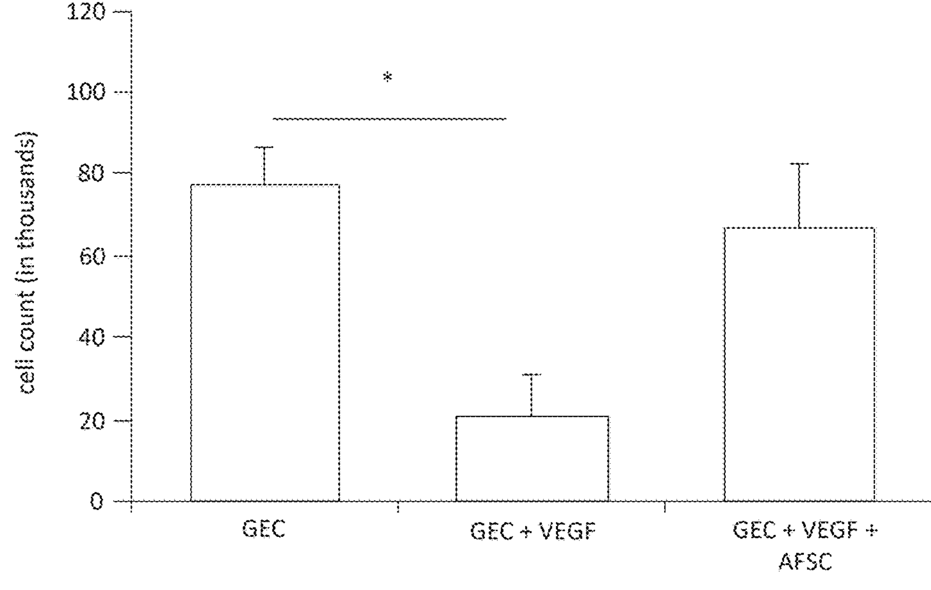
Figure 9K:
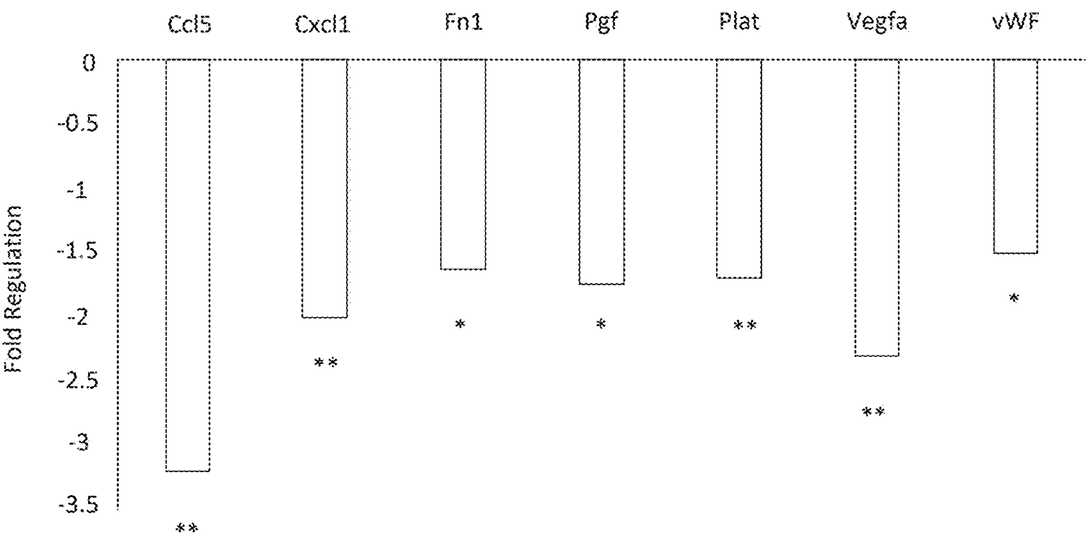

To verify that AFSC can mitigate GEC damage, co-culture assays were performed between AFSC and GEC (with no cell-cell contact) overexposed to VEGF for 24 h. High dose of VEGF exposure caused increased expression of VEGF, pVEGFR2 and VEGFR1 in GEC (FIG. 9A-B). After 24 hr of VEGF exposure, GEC demonstrated changes in pattern expression of VE-cadherin and CD31 (FIG. 9C-F) and decreased cellular proliferation that was rescued by AFSC (FIG. 9G-J). AFSC co-culture normalized increased expression of genes like VEGF, fibronectin and Ccl5 (FIG. 9K), thus protecting GEC from VEGF-induced damage.

Characterization of AFSC-Derived EVs

Figure 4A:
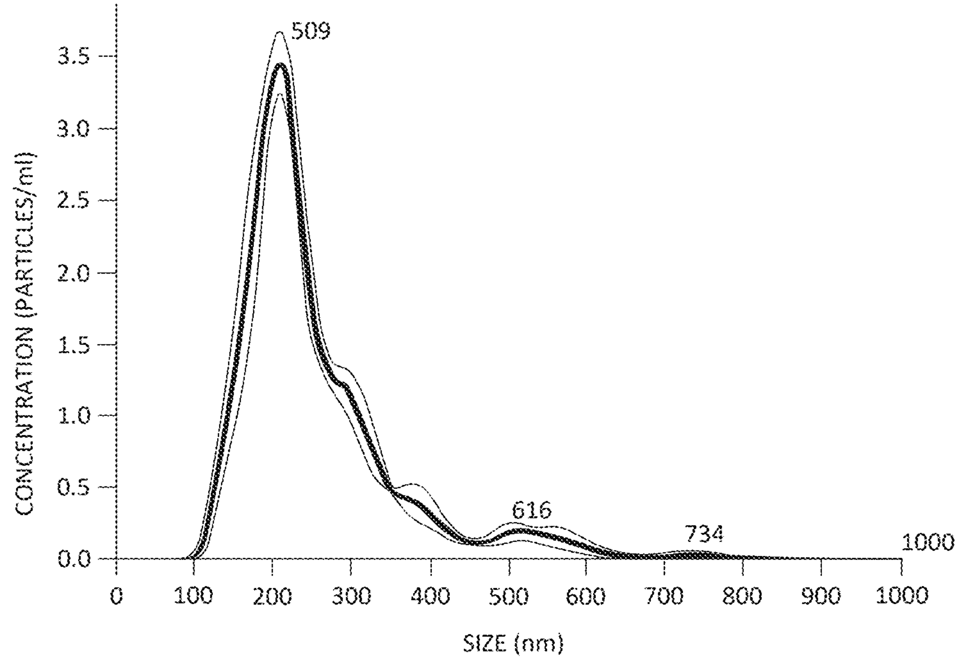
FIGS. 4A-D. AFSC-EV characterization. A. Graph representing Nanosight analysis of AFSC-derived EVs. The mean size and particle concentration are calculated by the Nanoparticle Tracking Analysis software. B. FACS analyses of AFSC-derived EVs showing the expression of mesenchymal (CD29, CD44, CD73, CD90, CD105 and CD146), exosomal (CD9, CD24 and CD63) and angiogenic related (CD202b, VEGFR1, VEGFR2, Neuropilin-I and Neuropilin-II) surface markers. Data are represented as the mean±SD of 4 different experiments. Dot lines indicate the isotopic controls, filled area the specific antibodies. C. Representative FACS graphs related to figure B. D. Western Blotting showing absence of VEGF (43 KDa, dimer) within AFSC-derived EVs compared to GEC used as control.
Figure 4B:
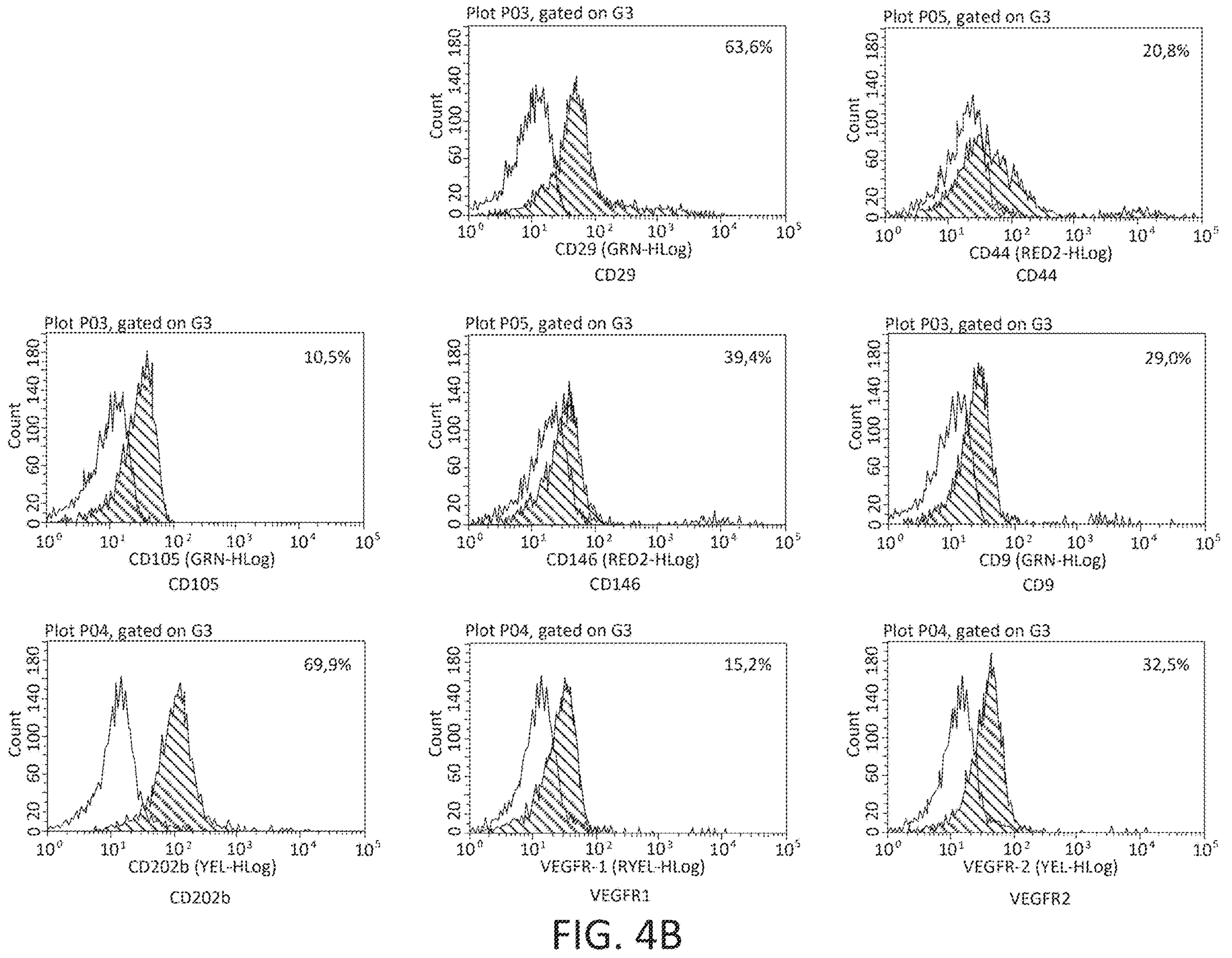
Figure 4B:
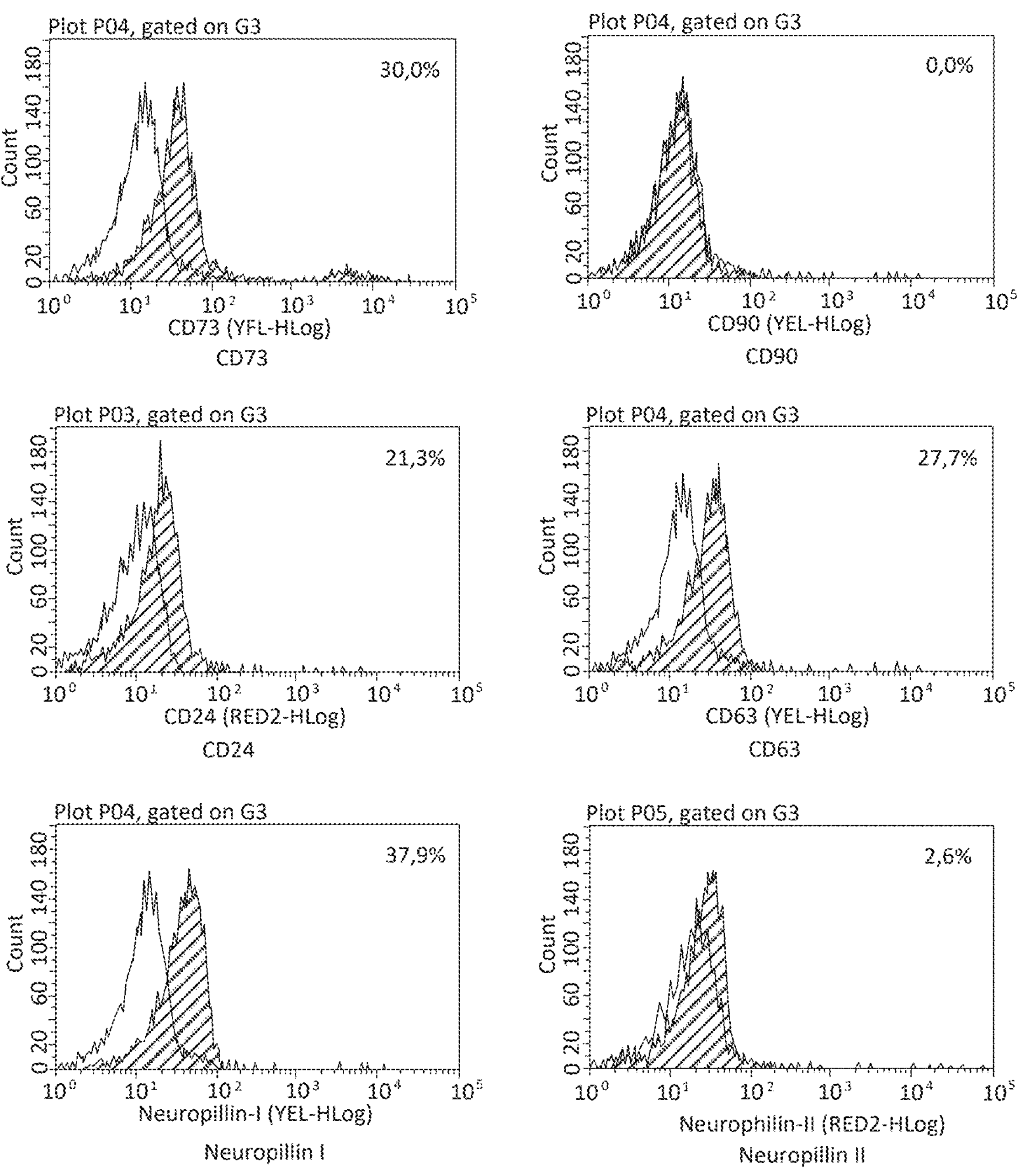
Figure 4C:
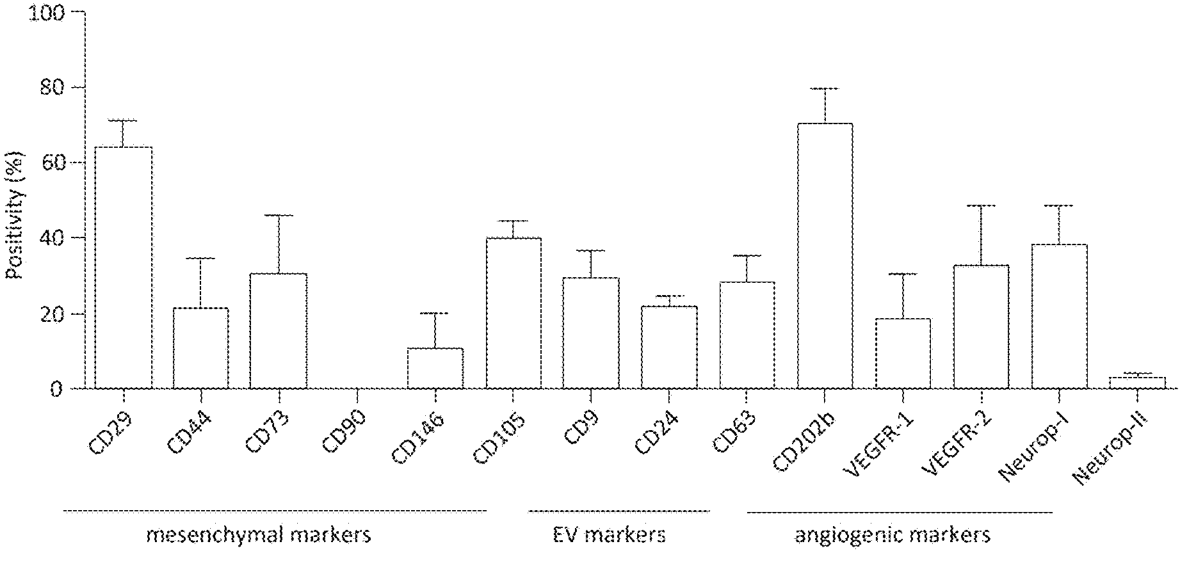
Figure 4D:
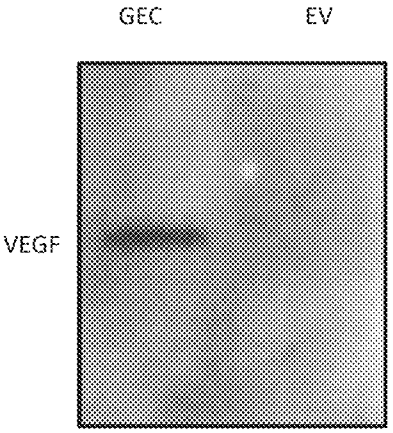
Figure 10A:
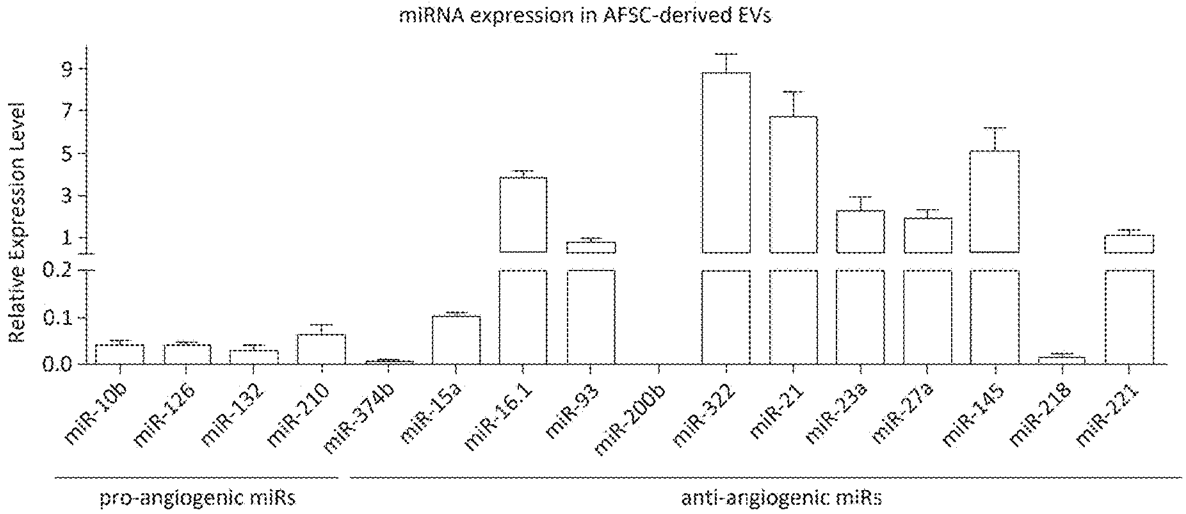
Figures 10B, 10C, 10D, 10E, 10F, 10G:
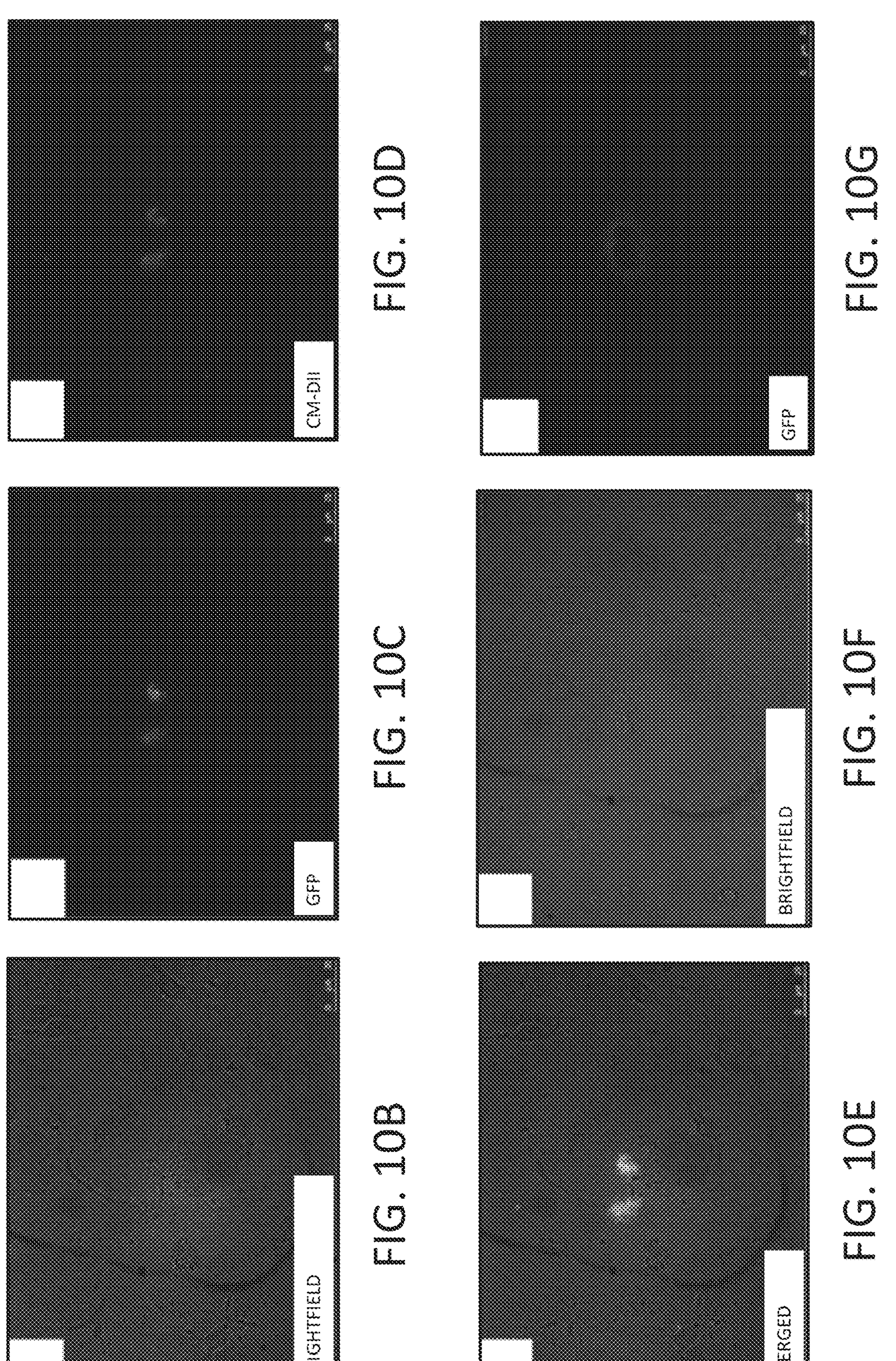
Figure 10H:
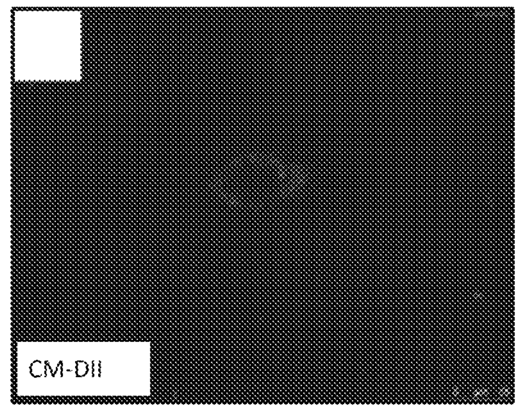
Figure 10I:
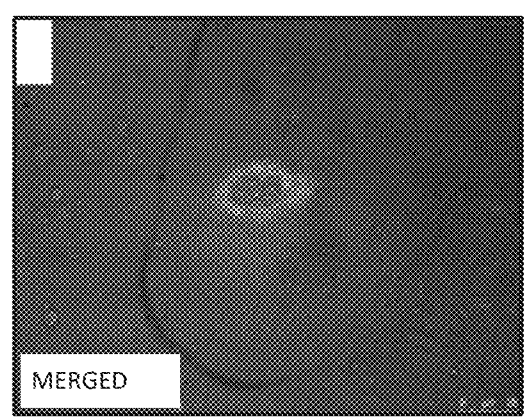

Since EVs have been established as an important mechanism of cell-to-cell communication (11-13), it was hypothesized that secretion of EVs from AFSC could be one of their mechanisms of action. In order to test the hypothesis, EVs from culture supernatants of AFSC were isolated by sequential ultracentrifugation. By Nanosight analysis, EVs were characterized as a heterogeneous population ranging from 100 nm to 400 nm in size (200.6±7.6 nm mode value), and their production in basal culture conditions appeared as roughly $2\times10^{10}$ EVs released by million cells in 24 hours (FIG. 4A). AFSC-derived EVs expressed surface markers typical of the cell of origin (CD73 and CD29) and CD24, a marker of amniotic fluid-derived exosomes (14) (FIG. 4B-C). EVs also expressed VEGFR1 and VEGFR2 (FIG. 4B-C) but did not contain VEGF (FIG. 4D). EVs contained miRNAs that specifically modulate VEGF/VGEFRs signaling (15) including miR-16.1, miR-23a, miR-27a, miR-93, miR-221, miR-145 and miR-322 (FIG. 10A).

To demonstrate that AFSC-derived EVs can be transferred to GEC, AFSC were transduced with LentiBrite GFP packaged lentiviral particles to constitutively express GFP and additionally tagged with CM-Dil. After overnight incubation with GECs, red/green EVs were found within the cytoplasm of GEC in proximity to the perinuclear zone (FIG. 10B-I).

AFSC-Derived EVs Contribute to VEGF Signaling Modulation in GEC

Figure 5A:
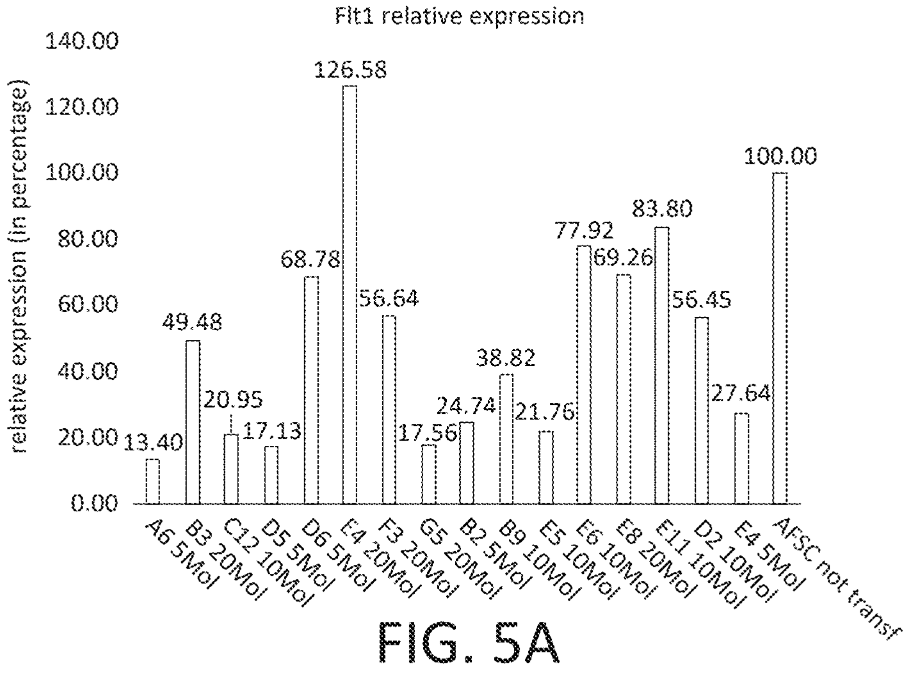
Figure 5B:
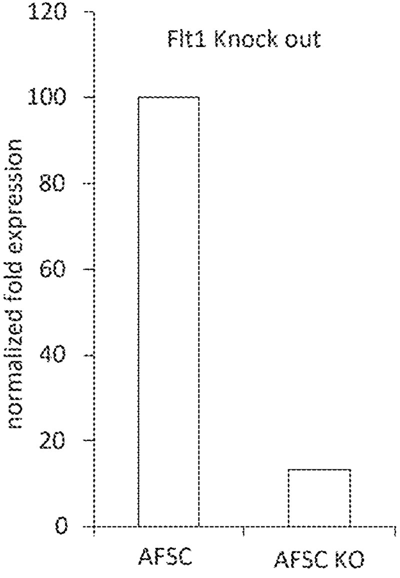
Figure 5C:
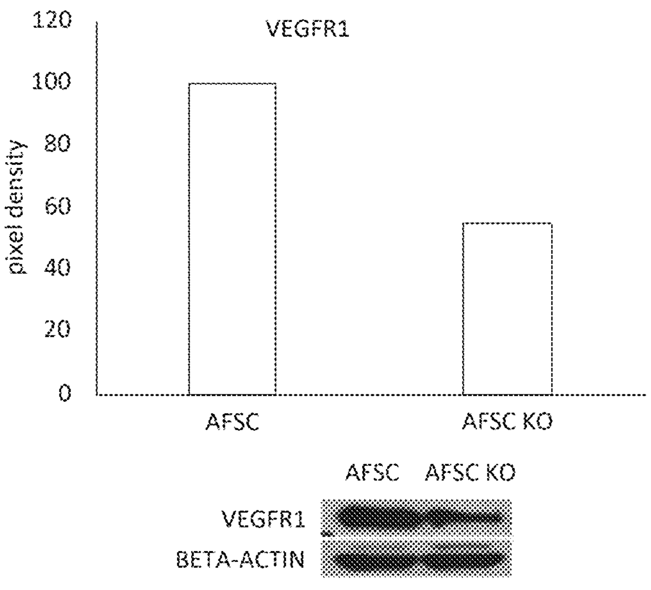
Figure 5D:
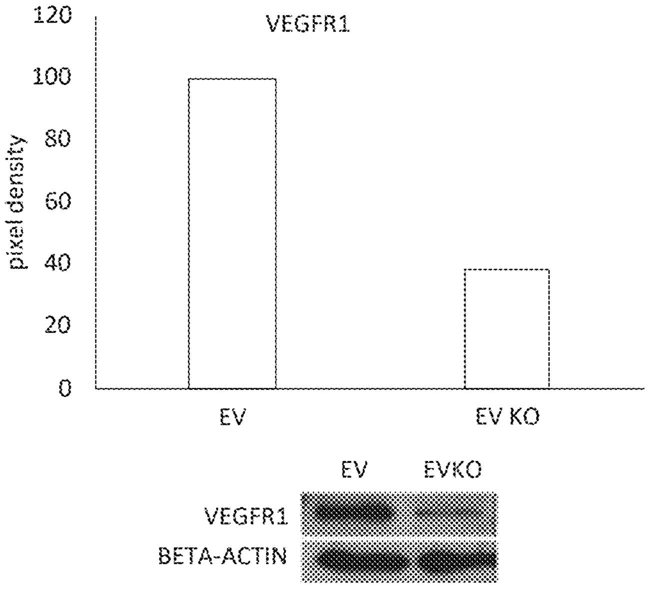
Figure 5E:
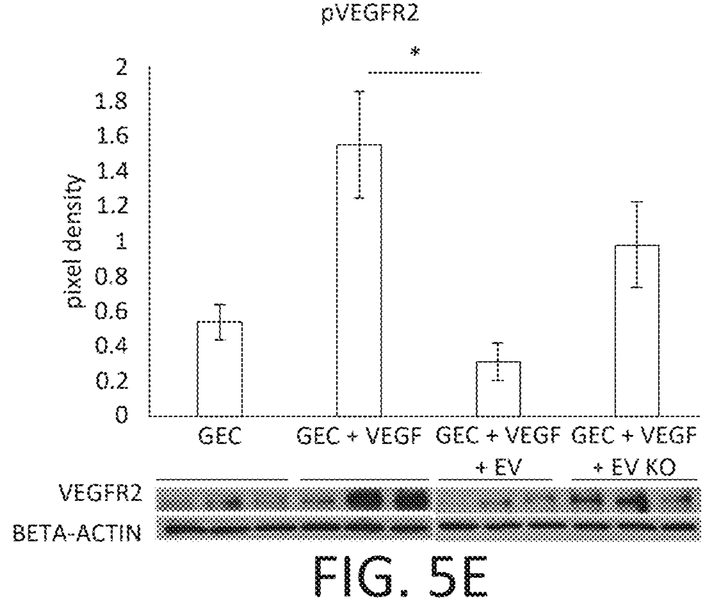
Figure 5F:
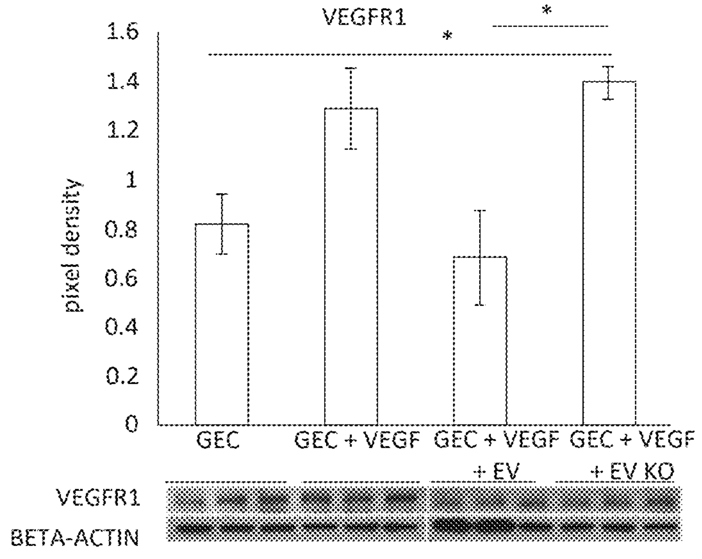

To demonstrate EV ability to modulate VEGF activity and confirm the potential role of VEGFR1 and sFlt1 in GEC damage/repair processes knock out (KO) EVs for Flt1 ($EV^{Flt-/-}$) were generated by transfecting AFSC using a shRNA Lentiviral Particles Transduction system. The clone with highest efficiency of transduction was used to derive and collect $EV^{Flt-/-}$. Both, KO AFSC and derived EVs showed reduced VEGFR1 expression (FIG. 5AD). After generation of the $EV^{Flt-/-}$, GEC was exposed to VEGF and treated them with EVs and KO EVs. Expression of pVEGFR2 and VEGFR1 was restored to baseline only in the presence of EVs (FIG. 5E-F), thus confirming that Flt1 plays a role in regulating VEGFR1 expression and VEGFR2 activity. Of note, slight differences in VEGFR1 level between in vitro and in vivo data can be attributed to the fact that in vivo data shows expression of all the glomerular cell types, including GEC, whereas in vitro data reflects only GEC response.

Interestingly, GEC exposed to EVs showed a higher presence of VEGF within the media (FIG. 6A) compared to GEC exposed to KO EV. These data suggest that EVs (that do not contain VEGF as reported above) could trap excess VEGF contained in the media, thus preventing its binding to VEGFRs on GEC resulting in decreased pVEGFR2 and VEGFR1 expression. To prove this a co-immunoprecipitation for VEGFR1 was performed on the same culture media and then probed for VEGF. Indeed, FIG. 6B shows lower level of VEGF in the experimental group with KO EVs compared to normal EVs. This data was confirmed independently using a different assay (FIG. 6C), where EVs and KO EVs were exposed to VEGF alone without GEC. Both these experiments confirmed that EVs can trap VEGF through VEGFR1, thus balancing VEGF signaling.

DISCUSSION

Various molecular signaling pathways contribute to the cell-cell communication between podocytes and GEC (1, 16) but VEGF expression plays a key role in the maintenance of the structure and function of glomerular capillaries including permeability and its alteration plays a major role in CKD (5). In normal animals, the blockade of VEGF correlates with GEC damage and an increase of proteinuria (17). On the contrary, in diabetic mice, VEGF is upregulated, and its blockade ameliorates diabetic albuminuria (18). Therefore, both deficiency and excess of VEGF appear to be detrimental to the physiological integrity of glomerular capillaries. An imbalance between VEGF and sFlt1 has been reported in many diseases, including the kidney (6-9), inducing widespread endothelial dysfunction, proteinuria and hypertension.

Accumulation of VEGF in human AS glomeruli was recently reported by Wang H et al. (19), thus suggesting a role of this signaling also in AS. The variation of the VEGF signaling during AS progression, including changes in sFlt1 expression, underlines the importance of VEGF within the glomerular microenvironment. However, the biological role of the VEGFR1/sFlt1 in the context of glomerular endothelial damage and its correlation to increased proteinuria are still unknown. Because GEC express an abundance of both VEGFR2 and VEGFR1, it is plausible that VEGFR1 and its soluble sFlt1 might have key importance in the regulation of the VEGF activity.

Indeed, in the animal model described herein it was found that VEGF is elevated particularly early in disease reaching the highest peak at 3 months of age, and is then decreased in more advanced stages. Interestingly, the level of sFlt1 within AS glomeruli also decreased over time, especially after the peak of VEGF expression, thus indicating that sFlt1 is not effectively counter-balancing VEGF increase gradually causing glomerular damage. In a study Quaggin's group (20) identified that podocytes produce sFlt1 and that elimination of sFlt1 in podocytes causes profound cellular damage and increases proteinuria. Since podocytes are the major producers of VEGF (2-3) within the glomerulus and that sFlt1 has autocrine activity on podocytes, a possible explanation for decreased VEGF and sFlt1 levels along disease progression might be attributed to loss of podocyte number in later stages of AS. Surprisingly, significant changes in pVEGFR2 and VEGFR1 expression were evident during the initial phase when podocyte loss is not predominant and proteinuria level is still low. These observations strongly suggest that in addition to the podocyte, which has been considered as the culprit of CKD progression (and this could be especially true in AS, where podocytes' inability to correctly assemble collIVα3,α4,α5 trimer leads to kidney failure (21)), the endothelium too could contribute to the initiation and progression of glomerular damage in AS and potentially in other forms of CKD.

Indeed, GEC damage represented by disruption of fenestration is very evident in 3 months old kidneys and with the use of Tek-Alport mice it was confirmed that GEC present abnormal VEGF signaling. Therefore, in early stages of AS disease, the elevated VEGF activity might play a role in promoting GEC damage thus in turn favoring podocyte injury and proteinuria. Interventions aimed at preventing early endothelial damage possibly by regulating VEGF expression, might represent an alternative to delaying disease progression in AS. It was previously shown that AFSC, when injected before the onset of proteinuria, are able to slow down disease progression in AS mice (10). Herein it was demonstrated that AFSC homed predominantly within the glomerulus of Alport mice and localized adjacent to the GEC, thus potentially triggering regulatory interaction in GEC. Once injected, AFSC decreased pVEGFR2 and increased VEGFR1 within the glomeruli, thus confirming that AFSC can modulate VEGF/VEGFRs activity. It was also previously reported that AFSC injection preserves podocyte number (10), which might account for the normalization of VEGF and sFlt1 levels observed in injected mice, as presented in the instant example. Preservation of podocyte number and regulation of VEGF and sFlt1 expression also correlated with improvement of kidney function.

Due to their close proximity to GEC, it was hypothesized that one of the possible mechanisms of renoprotection by AFSC could be via EV production. Recent studies have demonstrated that EVs released from cells are an integral component of the cell-to-cell communication network involved in tissue regeneration (11-13) and therefore may contribute to the paracrine action of stem cells in renal regeneration by directly activating target cells to secrete functionally active agents (12, 22).

Several groups have already demonstrated the in vivo ability of EVs derived from bone marrow mesenchymal stem cells to provide protection from acute kidney injury (23-26). Herein it is demonstrated that indeed AFSC do secrete EVs which expressed surface mesenchymal/exosomal markers and a number of angiogenic receptors, including VEGFRs.

It was demonstrated herein for the first time that EVs could function as a "trap" for excess VEGF by binding to VEGFR1 presented on the EVs surface. Thus, modulation of VEGF in AS glomeruli involves trapping of VEGF via the AFSC-derived EVs. In this context, the EVs presenting the VEGFR1 can counterbalance the decrease in sFlt1 observed during AS progression. Despite the higher presence of VEGFR2 over VEGFR1 in EVs, the affinity of the VEGF-VEGFR1 interaction is ten times stronger to that of between VEGF-VEGFR2, which further support the hypothesis (27). This mechanism of action can be potentially expanded to other molecules (such as TGFβ or ang II) since EVs present many different receptors. Downregulation of these molecules through "trapping" could be beneficial to resolving glomerular damage.

It was found that EVs contain miRs known to act in the modulation of VEGF levels (miR-16.1, -93), VEGF receptors (miR-16.1), and as positive and negative regulators of the VEGF signal transduction cascade (miR-23a, -27a, -221, -322 and -145) (15). These angiomodulatory cargo could involve potential new mechanisms of VEGF regulation, by triggering mechanisms of repair/regeneration at transcriptional level.

In conclusion, it was demonstrated that: 1. VEGF signaling plays an important role in disruption of glomerular homeostasis in AS and that injection of AFSC can restore the activity of this signaling possibly preventing further loss of kidney function; 2. Variation of the VEGF/sFlt1 signaling affects the endothelium in AS during the early stages when podocyte loss is not yet massive and proteinuria is low; 3. AFSC home within AS glomeruli in proximity to GEC and can secrete "angiomodulatory" EVs; and 4. AFSC-derived EVs can modulate VEGF signaling by trapping excess VEGF thorough VEGFR1-bonding.

Since AFSC localize within the glomeruli in the animal model, it is believed that the delivery of EVs by AFSC can specifically target the VEGF signaling in this renal compartment, thus favoring a local therapeutic action of VEGF where it is needed.

BIBLIOGRAPHY

1. Dimke, H, Maezawa, Y, Quaggin, SE: Crosstalk in glomerular injury and repair. Curr Opin Nephrol Hypertens, 24:231-238, 2015.
2. Fogo, A B, Kon, V: The glomerulus—a view from the inside—the endothelial cell. Int J Biochem Cell Biol, 42:1388-1397, 2010.
3. Cheng, H, Harris, R C: The glomerulus—a view from the outside—the podocyte. Int J Biochem Cell Biol, 42:1380-1387, 2010.
4. Eremina, V, Baelde, H J, Quaggin, S E: Role of the VEGF—a signaling pathway in the glomerulus: evidence for crosstalk between components of the glomerular filtration barrier. Nephron Physiol, 106: p 32-37, 2007.
5. Bartlett, C S, Jeansson, M, Quaggin, S E: Vascular Growth Factors and Glomerular Disease. Annu Rev Physiol, 78:437-461, 2016.
6. Eremina, V, Sood, M, Haigh, J, Nagy, A, Lajoie, G, Ferrara, N, Gerber, H P, Kikkawa, Y, Miner, J H, Quaggin, S E: Glomerular-specific alterations of VEGF-A expression lead to distinct congenital and acquired renal diseases. J Clin Invest, 111:707-716, 2003.
7. Zhai, Y L, Zhu, L, Shi, S F, Liu, L J, Lv, J C, Zhang, H: Elevated soluble VEGF receptor sFlt-1 correlates with endothelial injury in IgA nephropathy. PLOS One, 9: e101779, 2014.
8. Maynard, S E, Min, J Y, Merchan, J, Lim, K H, Li, J, Mondal, S, Libermann, T A, Morgan, J P, Sellke, F W, Stillman, I E, Epstein, F H, Sukbatme, V P, Karumanchi, S A: Excess placental soluble fms-like tyrosine kinase 1 (sFlt1) may contribute to endothelial dysfunction, hypertension, and proteinuria in preeclampsia. J Clin Invest, 111:649-658, 2003.
9. Kim, N H, Oh, J H, Seo, J A, Lec, K W, Kim, S G, Choi, K M, Baik, S H, Choi, D S, Kang, Y S, Han, S Y, Han, K H, Ji, Y H, Cha, D R: Vascular endothelial growth factor (VEGF) and soluble VEGF receptor FLT-1 in diabetic nephropathy. Kidney Int, 67:167-177, 2005.
10. Sedrakyan, S, Da Sacco, S, Milanesi, A, Shiri, L, Petrosyan, A, Varimezova, R, Warburton, D, Lemley, K V, De Filippo, R E, Perin, L: Injection of Amniotic Fluid Stem Cells Delays Progression of Renal Fibrosis. Journal of the American Society of Nephrology, 23:661-673, 2012.

11. Camussi, G, Deregibus, M C, Bruno, S, Cantaluppi, V, Biancone, L: Exosomes/microvesicles as a mechanism of cell-to-cell communication. Kidney Int, 78:838-848, 2010.

12. Lamichhane, T N, Sokic, S, Schardt, J S, Raiker, R S, Lin, J W, Jay, S M: Emerging roles for extracellular vesicles in tissue engineering and regenerative medicine. Tissue Eng Part B Rev, 21:45-54, 2015.

13. Nawaz, M, Fatima, F, Vallabhaneni, K C, Penfornis, P, Valadi, H, Ekström, K, Kholia, S, Whitt, J D, Fernandes, J D, Pochampally, R, Squire, J A, Camussi, G: Extracellular Vesicles: Evolving Factors in Stem Cell Biology. Stem Cells Int, 2016:1073140, 2016.

14. Keller, S, Rupp, C, Stoeck, A, Runz, S, Fogel, M, Lugert, S, Hager, H D, Abdel-Bakky, M S, Gutwein, P, Altevogt, P: CD24 is a marker of exosomes secreted into urine and amniotic fluid. Kidney Int, 72:1095-1102, 2007.

15. Dang, L T, Lawson, N D, Fish, J E: MicroRNA control of vascular endothelial growth factor signaling output during vascular development. Arterioscler Thromb Vasc Biol, 33:193-200, 2013.

16. Fogo, A B: Mechanisms of progression of chronic kidney disease. Pediatr Nephrol, 22:2011-2022, 2007.

17. Sugimoto, H, Hamano, Y, Charytan, D, Cosgrove, D, Kieran, M, Sudhakar, A, Kalluri, R: Neutralization of circulating vascular endothelial growth factor (VEGF) by anti-VEGF antibodies and soluble VEGF receptor 1 (sFlt-1) induces proteinuria. J Biol Chem, 278:12605-12608, 2003.

18. Sung, S H, Ziyadeh, F N, Wang, A, Pyagay, P E, Kanwar, Y S, Chen, S: Blockade of vascular endothelial growth factor signaling ameliorates diabetic albuminuria in mice. J Am Soc Nephrol, 17:3093-3104, 2006.

19. Wang, H, Yue, Z, Wu, J, Liu, T, Mo, Y, Jiang, X, Sun, L: The Accumulation of VEGFA in the Glomerular Basement Membrane and Its Relationship with Podocyte Injury and Proteinuria in Alport Syndrome. PLOS One, 10: e0135648, 2015.

20. Jin, J, Sison, K, Li, C, Tian, R, Wnuk, M, Sung, H K, Jeansson, M, Zhang, C, Tucholska, M, Jones, N, Kerjaschki, D, Shibuya, M, Fantus, I G, Nagy, A, Gerber, H P, Ferrara, N, Pawson, T, Quaggin, S E: Soluble FLT1 binds lipid microdomains in podocytes to control cell morphology and glomerular barrier function. Cell, 151: 384-399, 2012.

21. Kruegel, J, Rubel, D, Gross, O: Alport syndrome—insights from basic and clinical research. Nat Rev Nephrol, 9:170-178, 2013.

22. Sahoo, S, Klychko, E, Thorne, T, Misener, S, Schultz, K M, Millay, M, Ito, A, Liu, T, Kamide, C, Agrawal, H, Perlman, H, Qin, G, Kishore, R, Losordo, D W: Exosomes from human CD34 (+) stem cells mediate their proangiogenic paracrine activity. Circ Res, 109:724-728, 2011.

23. Bruno, S, Porta, S, Bussolati, B: Extracellular vesicles in renal tissue damage and regeneration. Eur J Pharmacol, 2016.

24. Gatti, S, Bruno, S, Deregibus, M C, Sordi, A, Cantaluppi, V, Tetta, C, Camussi, G: Microvesicles derived from human adult mesenchymal stem cells protect against ischaemia-reperfusion-induced acute and chronic kidney injury. Nephrol Dial Transplant, 26:1474-1483, 2011.

25. Bruno, S, Grange, C, Deregibus, M C, Calogero, R A, Saviozzi, S, Collino, F, Morando, L, Busca, A, Falda, M, Bussolati, B, Tetta, C, Camussi, G: Mesenchymal stem cell-derived microvesicles protect against acute tubular injury. J Am Soc Nephrol, 20:1053-1067, 2009.

26. Imberti, B, Morigi, M, Benigni, A: Potential of mesenchymal stem cells in the repair of tubular injury. Kidney Int Suppl (2011), 1:90-93, 2011.

27. Shibuya, M: Vascular Endothelial Growth Factor (VEGF) and Its Receptor (VEGFR) Signaling in Angiogenesis: A Crucial Target for Anti- and Pro-Angiogenic Therapies. Genes Cancer, 2:1097-1105, 2011.

28. Chiabotto, G, Bruno, S, Collino, F, Camussi, G: Mesenchymal Stromal Cells Epithelial Transition Induced by Renal Tubular Cells-Derived Extracellular Vesicles. PLOS One, 11: e0159163, 2016.

29. Da Sacco, S, Lemley, K V, Sedrakyan, S, Zanusso, I, Petrosyan, A, Peti-Peterdi, J, Burford, J, De Filippo, R E, Perin, L: A novel source of cultured podocytes. PLOS One, 8: e81812, 2013.

The embodiments are described in sufficient detail to enable those skilled in the art to practice the invention. Other embodiments may be utilized and formulation and method of using changes may be made without departing from the scope of the invention. The detailed description is not to be taken in a limiting sense, and the scope of the invention is defined only by the appended claims, along with the full scope of equivalents to which such claims are entitled.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

What is claimed is:

1. A method to ameliorate a symptom of treat Alport syndrome in a human subject comprising administering an effective amount of extracellular vesicles (EVs) isolated from human stem cells to a subject in need thereof, wherein the extracellular vesicles are administered intravenously or by local injection, wherein the stem cells are amniotic fluid stem cells (AFSCs).

2. The method of claim 1, wherein the EVs contain surface markers VEGFR1 and VEGFR2.

3. The method of claim 1, wherein the EVs contain surface markers CD73, CD29, CD24 or a combination thereof.

4. The method of claim 1, wherein the EVs do not contain VEGF.

5. The method of claim 1, wherein the EVs contain miR-16.1, miR-23a, miR-27a, miR-93, miR-221, miR-145, miR-322 or a combination thereof.

6. The method of claim 1, wherein the symptom is proteinuria.

* * * * *